United States Patent
Omiya

(10) Patent No.: US 6,755,785 B2
(45) Date of Patent: Jun. 29, 2004

(54) ULTRASONIC IMAGE GENERATING APPARATUS AND ULTRASONIC IMAGE GENERATING METHOD

(75) Inventor: Jun Omiya, Katano (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 10/299,463

(22) Filed: Nov. 19, 2002

(65) Prior Publication Data
US 2003/0120152 A1 Jun. 26, 2003

(30) Foreign Application Priority Data
Nov. 20, 2001 (JP) ........................................ 2001-355106

(51) Int. Cl.$^7$ ................................................ A61B 8/00
(52) U.S. Cl. ..................................................... 600/443
(58) Field of Search .................. 600/437, 490–441, 600/443, 447, 453–456

(56) References Cited

U.S. PATENT DOCUMENTS 4,937,797 A * 6/1990 Snyder et al. ............... 367/138

OTHER PUBLICATIONS

"Handbook of Ultrasonic Diagnostic Equipments", Colona Publishing Co., Ltd., pp. 37–42 and 91–94, (1985).

* cited by examiner

Primary Examiner—Francis J. Jaworski
(74) Attorney, Agent, or Firm—RatnerPrestia

(57) ABSTRACT

The ultrasonic image generating system has an ultrasonic beam output device which outputs a beam to a predetermined subject area, a receiving device which receives the reflected wave from the area, an image generating device which generates an image from the reflected wave and a beam output direction controller which performs control of changing the outgoing direction of the beam to the subject area based upon analysis of the image in order to reduce the area where the ultrasonic wave is shielded by an imaging target.

9 Claims, 28 Drawing Sheets

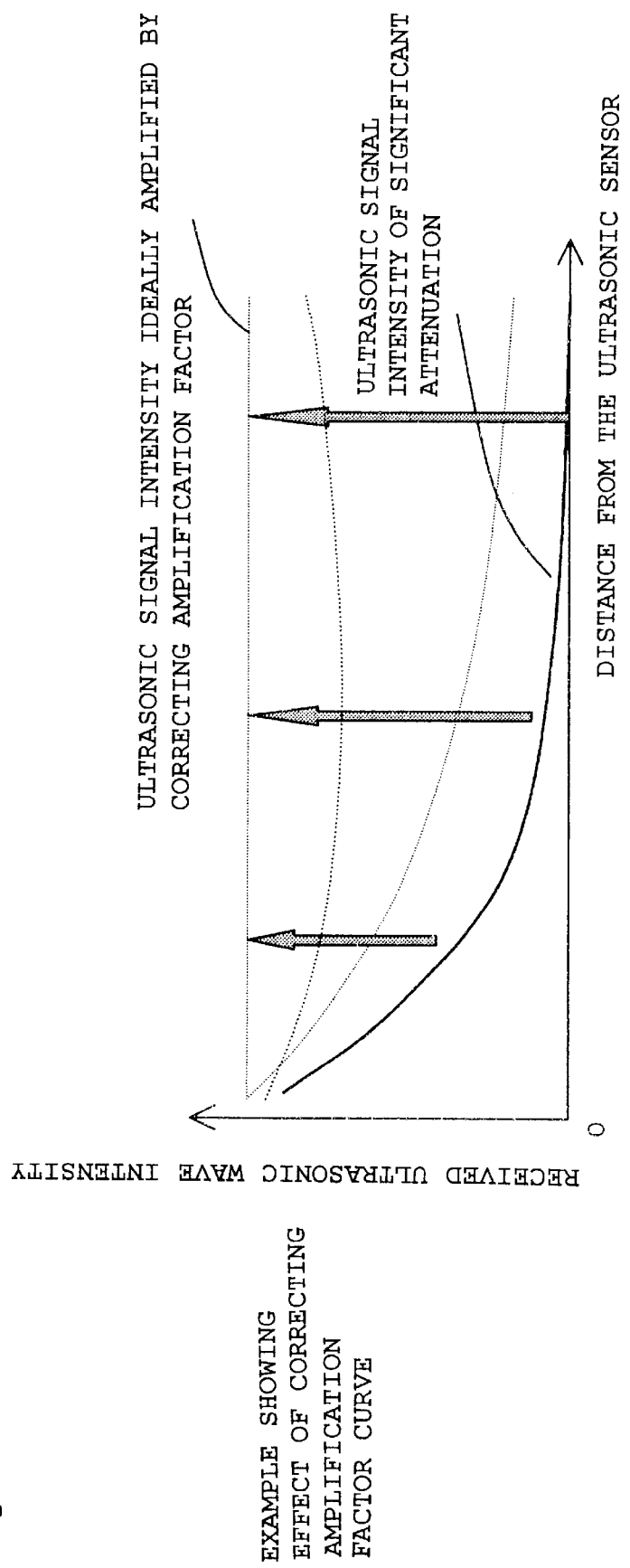

2400

ULTRASONIC IMAGE GENERATING APPARATUS AND ULTRASONIC IMAGE GENERATING METHOD

BACKGROUND OF THE INVENTION

1. Field of the Invention

The present invention relates to an ultrasonic image generating apparatus and an ultrasonic image generating method of generating an image based on a signal received from an ultrasonic sensor such as an ultrasonic apparatus.

2. Description of the Related Art

Apparatus sending sound, receiving a reflected wave from a subject and generating an image from a received signal thereof may be defined as an ultrasonic apparatus. The ultrasonic apparatus can conventionally obtain a two-dimensional tomographic image of an object non-invasively and in real time, and for instance, it has come into widespread use in clinical medicine as an indispensable apparatus because of its high safety to a living body, and the same advantages can be said in other fields.

In general, to generate the fault image, the ultrasonic apparatus receives an echo obtained by having a part of an ultrasonic wave sent from an ultrasonic probe (having an ultrasonic wave sending portion and a sound receiving portion) reflected in a change point (change face) of an organizational structure inside an object which is the subject (refer to Electric Industries Association of Japan Corporation, "Handbook of Ultrasonic Diagnostic Equipments", Colona Publishing, Co., Ltd. for instance).

Here, FIG. 27 schematically shows a structure of an ultrasonic wave sending portion and an ultrasonic wave receiving portion of an ultrasonic probe 2701. The ultrasonic wave sending portion and the ultrasonic wave receiving portion have the structure wherein a plurality of miniscule oscillation elements 2702 of generating the ultrasonic wave and receiving the ultrasonic wave to oscillate are arranged in one horizontal row. The ultrasonic wave sending portion is means of oscillating the ultrasonic wave from a row 2703 of a predetermined number (six in the drawing) of oscillation elements, and a wave front of the ultrasonic wave oscillated from each oscillation element forms one ultrasonic beam. At this time, a path length of the ultrasonic wave oscillated to a focus (or a focal range of a fixed length) of one ultrasonic beam from each oscillation element is different form one another. For instance, as shown in the drawing, in the row of oscillation elements 2703, a path length Pa of an oscillation element 2702a which is the closest to a focus 2704 is shorter than a path length Pb of an oscillation element 2702b which is the farthest from a focus 2704.

Thus, to form one ultrasonic beam, timing of ultrasonic wave oscillation of the oscillation element 2702b is rendered earlier than that of the oscillation element 2702a so that both ultrasonic waves simultaneously reach the focus 2704.

In the ultrasonic wave sending portion, the position of the row of oscillation elements 2703 is further moved from one end to the other end piece by piece of the oscillation element 2702. The ultrasonic beam thereby scans in the unit of the oscillation element 2702, so that an ultrasonic wave outgoing area substantially having a fixed width is formed. If there is the object in the ultrasonic wave outgoing area, the echo is generated on its surface and is received by the ultrasonic probe as ultrasonic wave receiving portion 2701 so that the fault image of the object is formed. Moreover, here, the ultrasonic wave receiving portion is the oscillation element 2702 functioning therein after outputting the ultrasonic wave. That is, the oscillation elements 2703 are used in common by the ultrasonic wave sending portion and the ultrasonic receiving portion.

As this reflected wave is of small magnitude compared to a sending wave, it is amplified when generating an image. To adjust this amplification degree, that is, to adjust image quality, a gain level is conventionally adjusted by a plurality (16 for instance) of sliders classified by depth of the object called STC (Sensitivity Time Control), which adjustment is manually performed by a user. In addition, it is also generally processed by a logarithm amplifier.

As described above, the amplification of the ultrasonic apparatus of the past is generally performed manually by the user while seeing a displayed image, starting with control of an STC level and a dynamic range However, there has been a problem that the aforementioned control of the image quality is complicated and requires experience. In addition, there are the cases where, depending on properties of an inspection subject, propagation of an ultrasonic signal is not good, a signal level of a received ultrasonic signal drops and the entire image cannot easily obtain contrast. Such problems on the image quality have sometimes taken a long time to solve because the work of displaying the image once, changing a parameter while seeing the image and approaching target image quality in order is necessary.

In addition, there has been the following problem. The ultrasonic wave generates the echo if it hits the change point (change plane) of the organizational structure inside an object which is the subject. At this time, behavior of the ultrasonic wave thereafter is different according to hardness of the organizational structure and so on.

For instance, in the case where a soft organization such as an internal organ is the object, a part of the ultrasonic wave is reflected on the change face but another part is further propagated beyond the change face. And in the case where there is a new object beyond it, the ultrasonic wave is reflected on the new object so as to form a further new image.

Yet, there are the cases where the entire ultrasonic wave is reflected on the surface of the object when a hard organization such as a bone or a stone is the object. To be more specific, as shown in FIG. 28, in the case where the entire ultrasonic wave striking a change face 2803 of an object 2802 is reflected on the side of the probe in an imaging subject area 2801 formed by the ultrasonic beam emitted from the ultrasonic probe 2701, the area right behind the object 2802 becomes a shielded area 2804 passed through by no ultrasonic beam and having no information as the image. Therefore, it is not possible to know what is there, and for instance, whether or not there is further an object which is the subject.

To delete the disadvantage, the user has only to change a position of the ultrasonic probe 2701. To do so, however, the user needs to visually check on the screen to see which portion of the image is the shielded area 2804, and it takes time and effort. In addition, correspondence between an original image and the image after changing the position of the ultrasonic probe 2701 becomes unclear, and so reliability of obtainable information as a whole is reduced.

SUMMARY OF THE INVENTION

An object of the present invention is, in consideration of such problems of an image display apparatus of the past, to obtain the ultrasonic image generating apparatus and the ultrasonic image generating method capable of thoroughly obtaining the image in an imaging area while saving time and effort for operation on the user side and reducing the area where the ultrasonic wave is shielded by an imaging target.

Another object of the invention is to provide the image display apparatus and so on capable of adjusting the image quality in real time and performing the work of image adjustment which required experience in the past automatically and in a short time.

The 1st invention of the present invention is an ultrasonic image generating apparatus comprising:

ultrasonic beam outputting means of outputting an ultrasonic beam to a predetermined subject area;

ultrasonic beam receiving means of receiving a reflected ultrasonic beam which is a reflected wave of said ultrasonic beam obtained from said subject area;

image generating means of generating an image based on the reflected ultrasonic beam received by said ultrasonic beam receiving means; and ultrasonic beam output direction controlling means of performing control of changing an outgoing direction of the ultrasonic beam of said ultrasonic beam outputting means to said subject area.

The 2nd invention of the present invention is the ultrasonic image generating apparatus according to the 1st invention, wherein said ultrasonic beam output direction controlling means electrically controls said change.

The 3rd invention of the present invention is the ultrasonic image generating apparatus according to the 1st invention, further comprising image analyzing means of analyzing the image generated by said image generating means, wherein the ultrasonic beam output direction controlling means controls said change based on analysis results of said image analyzing means.

The 4th invention of the present invention is the ultrasonic image generating apparatus according to the 3rd invention, wherein said image analyzing means analyzes whether or not there is a predetermined imaging target in said subject area, and in the case where there is said imaging target, analyzes whether or not there is a shielded area in which said ultrasonic beam is shielded by said imaging target in said subject area, and in the case where there is said shielded area, said ultrasonic beam output direction controlling means controls said change so that the area to be passed through by the ultrasonic beam emitted from said ultrasonic beam outputting means next includes a part of said shielded area.

The 5th invention of the present invention is the ultrasonic image generating apparatus according to the 1st invention, further comprising reflected ultrasonic beam analyzing means of analyzing the reflected ultrasonic beam received by said ultrasonic beam receiving means, wherein said ultrasonic beam output direction controlling means controls said change based on analysis results of said reflected ultrasonic beam analyzing means.

The 6th invention of the present invention is the ultrasonic image generating apparatus according to the 5th invention, wherein said reflected ultrasonic beam analyzing means analyzes whether or not there is a non-detected area in which no reflected ultrasonic beam is detected in said subject area, and in the case where there is said non-detected area, said ultrasonic beam output direction controlling means controls said change so that the area to be passed through by the ultrasonic beam emitted from said ultrasonic beam outputting means next includes a part of said non-detected area.

The 7th invention of the present invention is the ultrasonic image generating apparatus according to the 6th invention, wherein said subject area is determined to be within a distance capable of detecting said reflected ultrasonic beam at a predetermined intensity.

The 8th invention of the present invention is an ultrasonic image generating method comprising:

an ultrasonic beam outputting step of outputting an ultrasonic beam to a predetermined subject area;

an ultrasonic beam receiving step of receiving a reflected ultrasonic beam which is a reflected wave of said ultrasonic beam obtained from said subject area;

an image generating step of generating an image based on the reflected ultrasonic beam received by said ultrasonic beam receiving step; and an ultrasonic beam output direction controlling step of performing control of changing an outgoing direction of the ultrasonic beam of said ultrasonic beam outputting step to said subject area.

The 9th invention of the present invention is the ultrasonic image generating method according to the 8th invention, wherein said ultrasonic beam output direction controlling step electrically controls said change.

The 10th invention of the present invention is the ultrasonic image generating method according to the 8th invention, further comprising an image analyzing step of analyzing the image generated by said image generating step, and wherein the ultrasonic beam output direction controlling step controls said change based on analysis results thereof.

The 11th invention of the present invention is the ultrasonic image generating method according to the 8th invention, further comprising a reflected ultrasonic beam analyzing step of analyzing the reflected ultrasonic beam received by said ultrasonic beam receiving step, and wherein said ultrasonic beam output direction controlling step controls said change based on analysis results thereof.

The 12th invention of the present invention is a program of causing a computer to function as the image analyzing means of analyzing the image generated by said image generating means of the ultrasonic image generating apparatus according to the 3rd invention and the ultrasonic beam output direction controlling means of controlling said change based on the analysis results of said image analyzing means.

The 13th invention of the present invention is a program of causing a computer to function as the reflected ultrasonic beam analyzing means of analyzing the reflected ultrasonic beam received by said ultrasonic beam receiving means of the ultrasonic image generating apparatus according to the 5th invention and the ultrasonic beam output direction controlling means of controlling said change based on the analysis results of said reflected ultrasonic beam analyzing means.

The 14th invention of the present invention is a medium having a program according to the 12th invention and processable by a computer.

The 15th invention of the present invention is a medium having a program according to the 13th invention and processable by a computer.

BRIEF DESCRIPTION OF THE DRAWINGS

FIG. 6 is a diagram showing an effect of correcting an amplification factor obtained by the ultrasonic image generating apparatus according to the fourth embodiment of the present invention;

DESCRIPTION OF SYMBOLS

Figure 1:
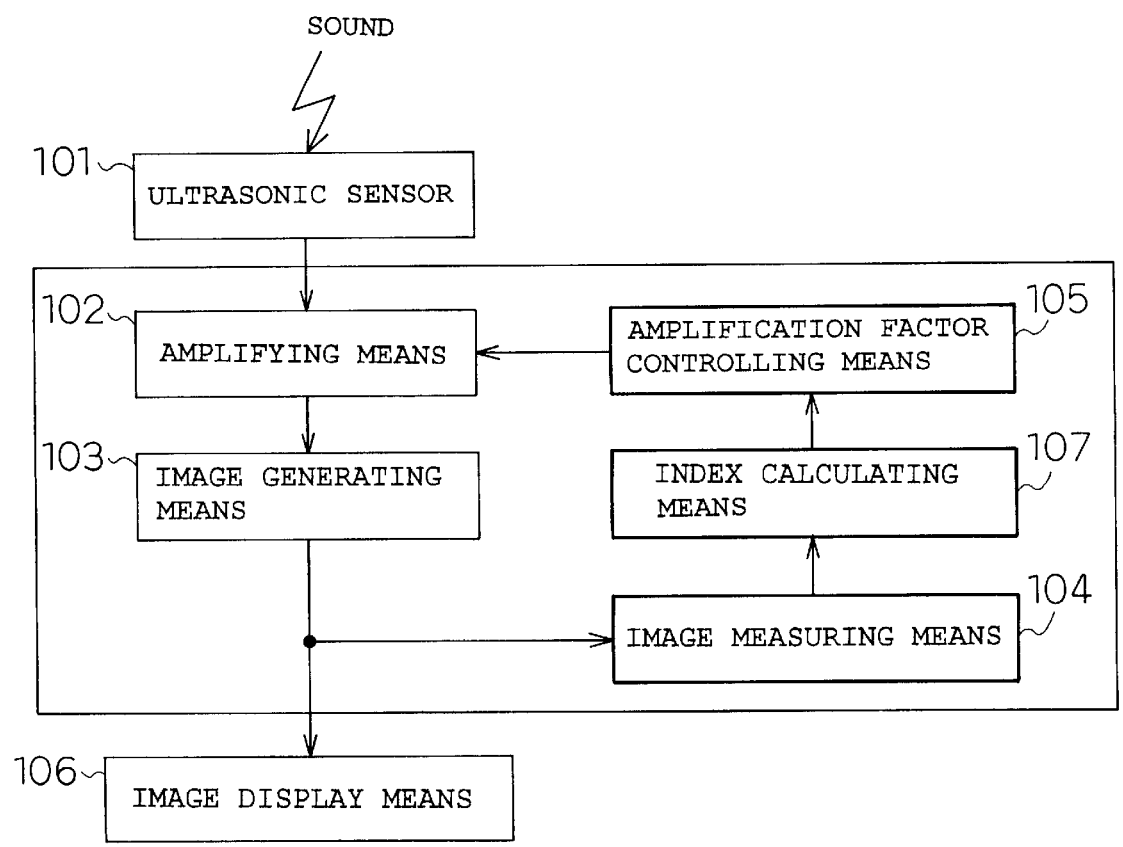
FIG. 1 is a block diagram showing a configuration of an ultrasonic image generating apparatus according to a fourth embodiment of the invention.

101 Ultrasonic sensor
102 Amplifying means
103 Image generating means
104 Image measuring means
105 Amplification factor controlling means
106 Image display means
107 Index calculating means
201 Ultrasonic wave sending portion controlling means
202 Ultrasonic wave sending portion
301 Image generating arithmetic section
302 Frame memory
303 Arithmetic processing section
304 Arithmetic controlling section
1600 Ultrasonic image generating apparatus
1601 Ultrasonic wave receiving portion
1602 Amplifying means
1603 Image generating means
1604 Image analyzing means
1605 Image display means
1606 Ultrasonic wave sending portion
1607 Ultrasonic beam output direction controlling means
1608 Condition setting means

DETAILED DESCRIPTION OF THE PREFERRED EMBODIMENTS

Hereafter, embodiments of the present invention will be described by referring to the drawings.

(First Embodiment)

Figure 16:
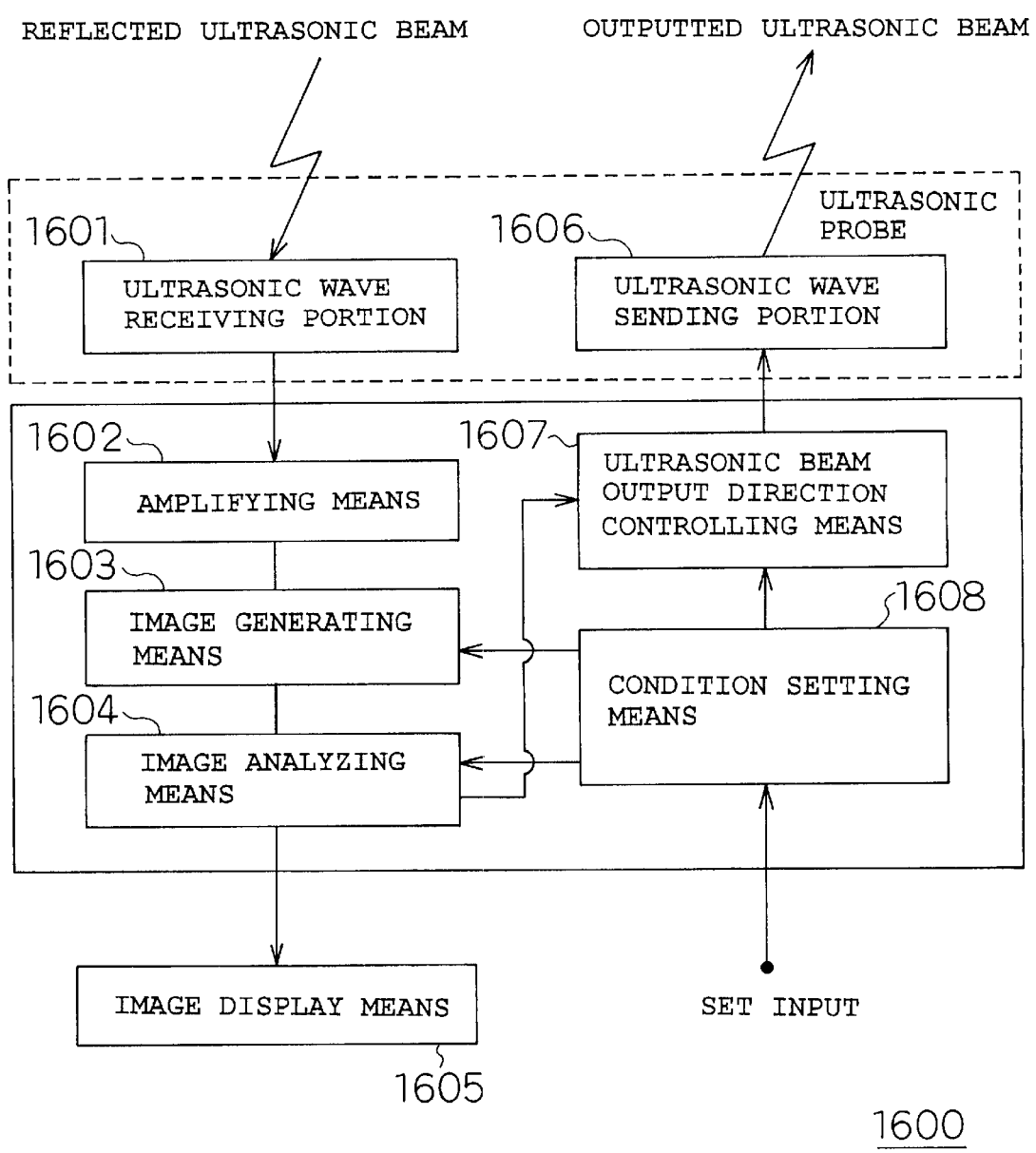
FIG. 16 is a block diagram showing a configuration of the ultrasonic image generating apparatus according to a first embodiment of the present invention.

FIG. 16 shows a schematic block diagram of an ultrasonic image generating apparatus according to a first embodiment of the present invention. As shown in the drawing, in an ultrasonic image generating apparatus 1600, an ultrasonic wave receiving portion 1601 is means of receiving an ultrasonic wave (reflected ultrasonic beam) reflected from an object, amplifying means 1602 is an amplifier of performing signal processing for general image configuration such as signal amplification. Image generating means 1603 is means of generating an image from sound information and writing image data to a storage device such as a frame memory which is not shown. Image analyzing means 1604 is means of analyzing image data. Image display means 1605 is means of displaying the image data in the image generating means 1603.

Figure 27:
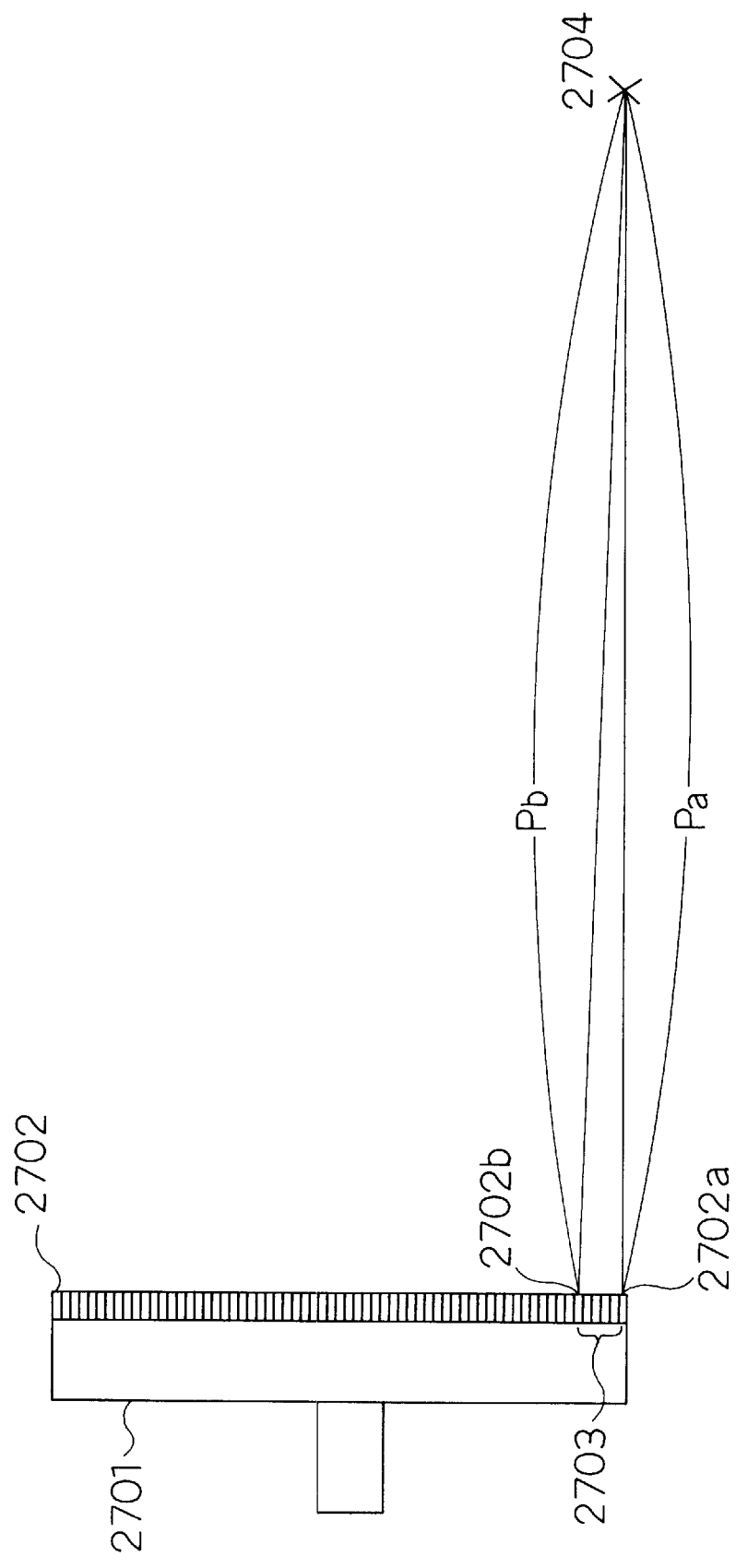
FIG. 27 is a diagram for explaining the operation of the ultrasonic image generating apparatus according to the prior art.
Figure 28:
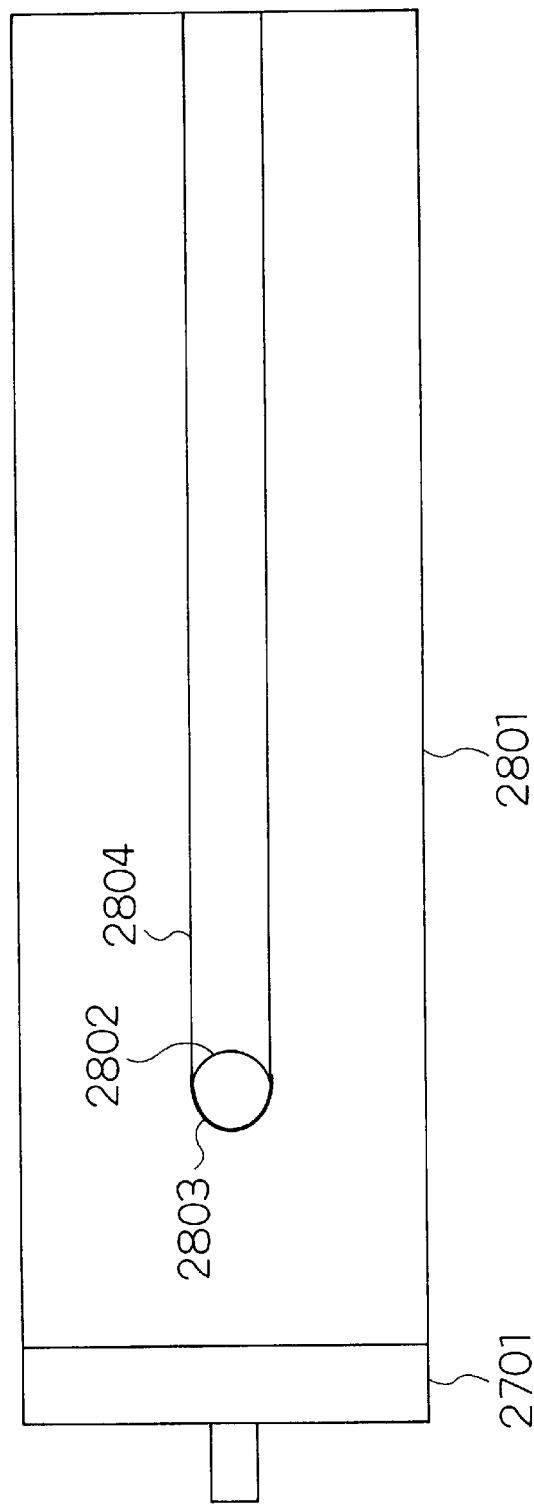
FIG. 28 is a diagram for explaining the operation of the ultrasonic image generating apparatus according to the prior art.

Next, an ultrasonic wave sending portion 1606 is means of outputting an ultrasonic wave (ultrasonic beam) to an imaging subject, ultrasonic beam output direction controlling means 1607 is means of controlling a direction of the ultrasonic beam outputted by the ultrasonic wave sending portion 1606 based on analysis results of the image analyzing means 1604, condition setting means 1608 is means of setting operating conditions of the image generating means 1603, image analyzing means 1604 and ultrasonic beam output direction controlling means 1607 based on setting input from the outside. Moreover, the ultrasonic wave receiving portion 1601 and the ultrasonic wave sending portion 1606 constitute an ultrasonic probe 1801 shown in FIG. 18, and a detailed configuration of the ultrasonic wave sending portion 1606 and the ultrasonic wave receiving portion 1601 is the one wherein a row of oscillation elements is shared and switched its role for each operation as with a past example shown in FIG. 27.

Figure 17:
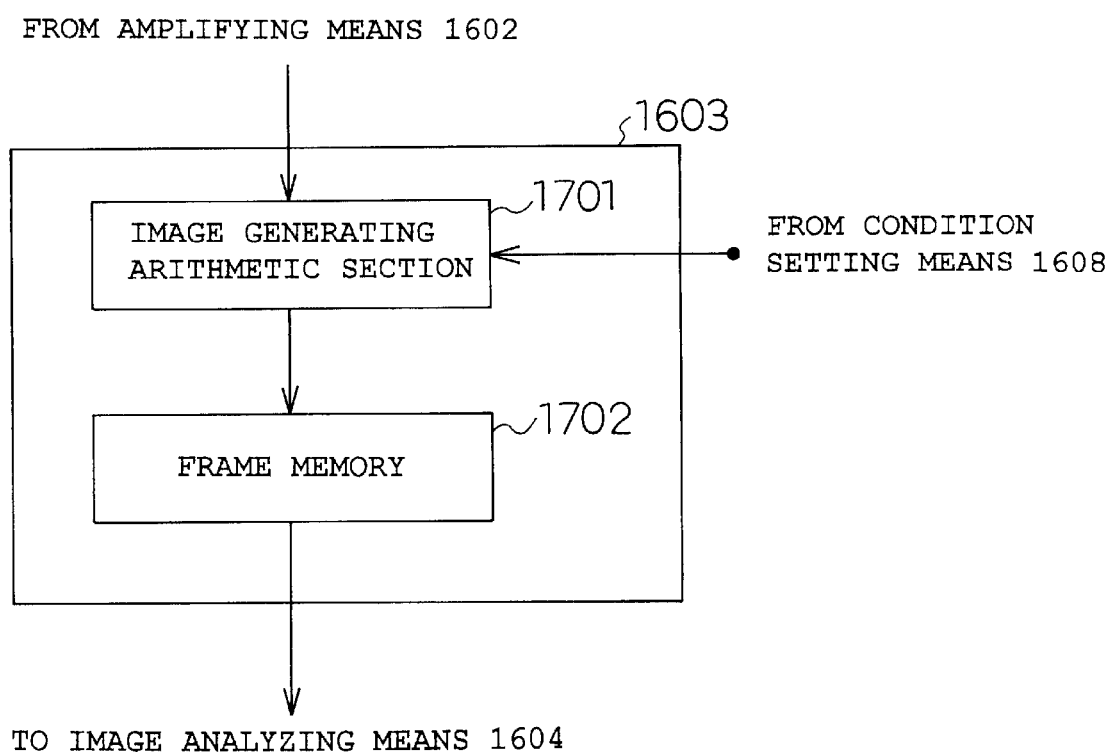
FIG. 17 is a block diagram showing the configuration of image generating means of the ultrasonic image generating apparatus according to the first embodiment of the present invention.

In addition, as shown in FIG. 17, the image generating means 1603 is comprised of an image generating arithmetic section 1701 of collecting a plurality of pieces of ultrasonic wave data which is one-dimensional data and arranging them in a predetermined order to generate two-dimensional data, and a frame memory 1702 of holding the generated image data. In the image generating arithmetic section 1701, rearrangement of the collected plurality of pieces of ultrasonic wave data and interpolating calculation in conjunction therewith are performed.

Operation of the ultrasonic image generating apparatus according to the first embodiment of the present invention having the above configuration will be described below, and one embodiment of the ultrasonic image generating method of the present invention will also be described thereby. Moreover, the following description is given on the assumption that the imaging subject of the ultrasonic image generating apparatus is a human body organization.

First of all, a user determines the direction of the ultrasonic probe 1801 to a desired imaging subject area as an initial state, and fixes the probe so that it will not move. The ultrasonic beam outgoing direction of the ultrasonic beam output direction controlling means 1607 is also set in one predetermined direction. Next, the ultrasonic beam is outputted to the imaging area from the ultrasonic wave sending portion 1606 of the ultrasonic probe 1801. In the case where there is the object in the imaging subject area, the ultrasonic beam reflected on it is received as the reflected ultrasonic beam by the ultrasonic wave receiving portion 1601. The received reflected ultrasonic beam is sent as the ultrasonic wave data to the amplifying means 1602, where it is amplified and then inputted to the image generating means 1603. In the image generating means 1603, the image generating arithmetic section 1701 sequentially accumulates the amplified ultrasonic wave data and rearranges it in a two-dimensional array so as to generate an image. The generated image is sent to the frame memory 1702 in order to output it to the image analyzing means 1604. The image stored in the frame memory 1702 is outputted to the image analyzing means 1604.

Figure 18:
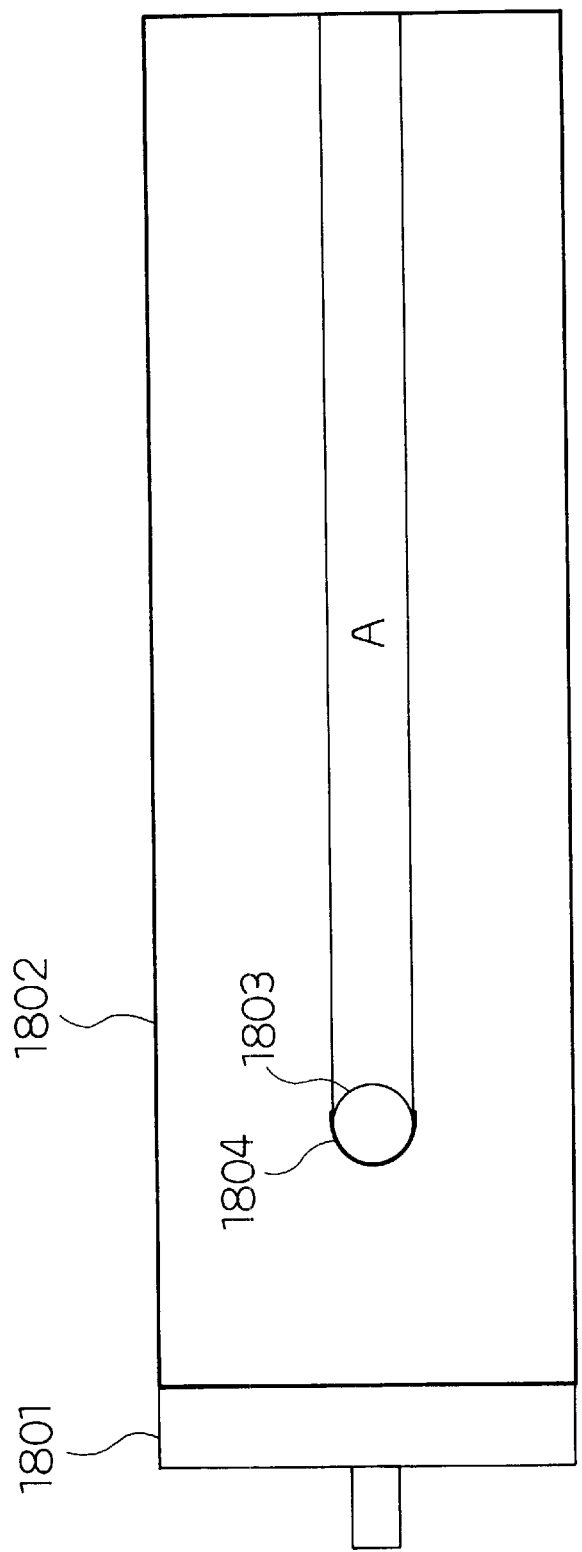
FIG. 18 is a diagram for explaining operation of the ultrasonic image generating apparatus according to the first to third embodiment of the present invention.

Here, the ultrasonic image displayed by the above operation in the initial state is schematically shown in FIG. 18. As shown in the drawing, an imaging subject area 1802 (the portion enclosed with a thick black line in the drawing) is formed by a scan of the ultrasonic beam outputted from the ultrasonic probe 1801. The imaging subject area 1802 is a rectangle of which short side is a width of the ultrasonic probe 1801 and long side is a critical distance capable of obtaining the image at fixed brightness by the reflected ultrasonic beam. Moreover, the critical distance is set by picking up the image of a test object of which internal structure and material are known with the ultrasonic beam and based on the brightness of a fault image of that substance. In addition, in the case of using a human body as the test object, it is desirable to use a body part in the proximity of the body part to be the imaging subject area 1802 and of which information on the inside is known in advance.

If an imaging object 1803 is in the imaging subject area 1802, the ultrasonic beam is reflected on a change face 1804 thereof. If the imaging object 1803 has sufficient hardness and totally reflects a crashed ultrasonic beam in substance, the ultrasonic beam is shielded and a shielded area A is formed in the rear of the imaging object 1803 seen from the ultrasonic probe 1801. On the other hand, the areas other than the shielded area A include information on the object reflecting only a part of the crashed ultrasonic beam and irregular reflection of internal organization, so that they are shown to be visible as image information having at least the brightness of the critical distance or higher.

Next, the image analyzing means 1604 analyzes the ultrasonic image shown in FIG. 18, and detects the shielded area A. The detection is performed as follows. First, the image analyzing means 1604 measures the brightness of the imaging subject area 1802, and detects a portion having the brightness of a predetermined first reference value or more as the change face 1804 (the portion enclosed with a thick black line in the drawing) of the object 1803. After detecting the change face 1804, the image analyzing means 1604 measures the brightness of a surrounding portion thereof, and in the case where there is a difference of a predetermined second reference value or more between the brightness of the change face 1804 and that of the surrounding portion, it determines that the object 1803 is in the area including the change face.

Furthermore, the image analyzing means 1604 measures the brightness of the surrounding portion of the area regarded as the object 1803, and in the case where there is an area having the brightness equal to or less than that of the above critical distance, it is detected as the shielded area A where the ultrasonic beam is shielded by the object 1803. At this time, the shielded area A is detected as the area reaching the farthest portion of the imaging subject area 1802. The image analysis results including coordinates defining the shielded area A are outputted to the ultrasonic beam output direction controlling means 1607.

Figure 19:
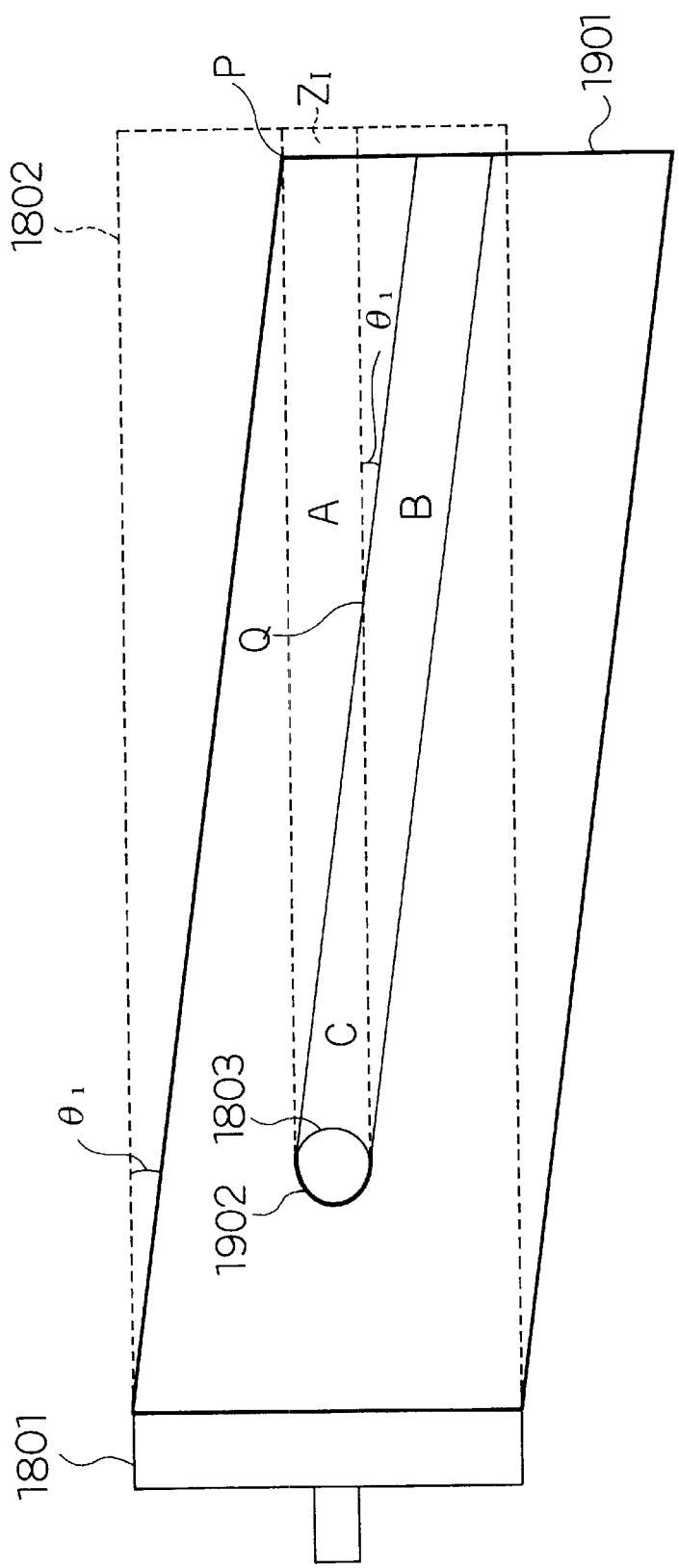
FIG. 19 is a diagram for explaining the operation of the ultrasonic image generating apparatus according to the first to third embodiment of the present invention.

On receiving the image analysis results, the ultrasonic beam output direction controlling means 1607 changes an ultrasonic beam output direction of the ultrasonic beam output direction controlling means 1607 from the initial state based on the results. This change is made so that the imaging subject area (excluding the shielded area) formed by the ultrasonic beam to be outputted covers to a maximum the shielded area A of the image picked up last time. To be more specific, as shown in FIG. 19, an outgoing angle of the ultrasonic beam is rotated by an angle $\theta_1$ so that the long side of a new imaging subject area 1901 matches with a boundary portion P between the imaging subject area 1901 and the shielded area A of the image picked up last time while keeping the length thereof, that is, the critical distance fixed.

Figure 26:
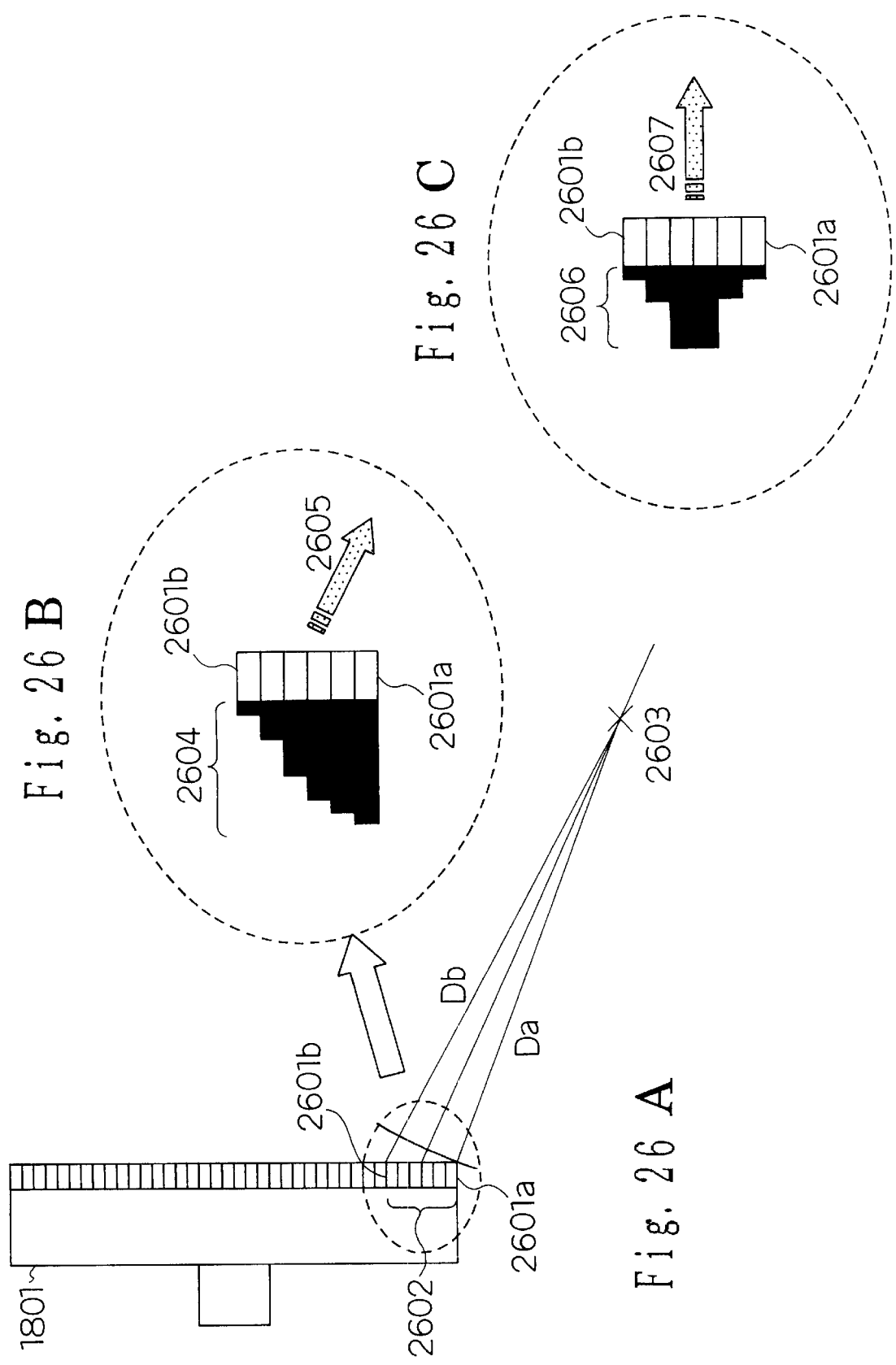
FIG. 26A is a diagram for explaining the operation of the ultrasonic image generating apparatus according to the first to third embodiment of the present invention.
FIG. 26B is a diagram for explaining the operation of the ultrasonic image generating apparatus according to the first to third embodiment of the present invention.
FIG. 26C is a diagram for explaining the operation of the ultrasonic image generating apparatus according to the first to third embodiment of the present invention.

Here, rotation control of the outgoing angle of the ultrasonic beam will be described. As shown in FIG. 26 and as described in Description of the Related Art, the ultrasonic wave sending portion 1606 of the ultrasonic probe 1801 has the structure wherein a plurality of oscillation elements 2601 are arranged in one horizontal row so as to oscillate the ultrasonic wave from the row of the predetermined number of oscillation elements and form one ultrasonic beam. At this time, to change a direction (an angle made with a normal to a row of oscillation elements 2602) of a focus (or a focal range of a fixed length) of one ultrasonic beam is performed by changing a delay amount of oscillation time of each oscillation element.

As shown in FIG. 26A, thought is given to the case where the ultrasonic beam is oscillated to a focus 2603 by oscillating the row of oscillation elements 2602. If the distance between the focus 2603 and an oscillation element 2601a which is at the closest position, of the row of oscillation elements 2602, to the focus 2603 is Da, a delay amount 2603 of the oscillation time of each oscillation element is controlled so that, when the oscillation element 2601a is oscillated, the ultrasonic wave oscillated by an element other than the oscillation element 2601 of the row of oscillation elements 2602 reaches a circumference of a circle of a radius Da centering on the focus 2603. This state is shown in FIG. 26B.

Such delay control is performed so that the ultrasonic beam oscillated by the oscillation element 2602 proceeds in a direction 2605 and converges on the focus 2603.

Moreover, FIG. 26C shows distribution of the delay amounts in the case of outputting the ultrasonic beam in a front direction 2607 of the row of oscillation elements 2602. It can be seen, compared to FIG. 26B, that the difference in setting of the delay amount is definite.

On the other hand, it is the same in case of receiving the ultrasonic beam reflected on the focus 2603. In case of receiving, the ultrasonic wave concentrically spreading from the focus is received, so that an oscillation element 1601 receives a receiving wave earliest, and the oscillation element 2601 receives it lastly.

The ultrasonic wave receiving portion 1601 converts the difference in the distance from the focus 2603 to each individual oscillation element of the row of oscillation elements 2602 into delay time (the oscillation element having received it early is given a large delay amount and the one having received it late is given a small delay amount) so that phases of the ultrasonic wave received by each oscillation elements are put in order and synthesized as a received ultrasonic beam.

It is possible, by the above operation, to change only the direction of the emitted ultrasonic beam while keeping the position of the ultrasonic probe fixed.

Hereafter, to form the new imaging subject area 1901 from the ultrasonic wave sending portion 1606 of the ultrasonic probe 1801, the ultrasonic beam of which outgoing angle is changed is outputted and the same image generating operation as above is performed, and the ultrasonic image in the imaging subject area 1901 in FIG. 19 is obtained.

In the new imaging subject area 1901, the image information on the areas excluding a shielded area B is obtained. As the ultrasonic beam is inclined to the object 1803 by the angle $\theta_1$ and strikes on a change face 1902, the newly formed shielded area B also intersects with the shielded area A at the angle $\theta_1$, and includes a shared area C overlapping the shielded area A.

The shielded area B is divided into the area overlapping the imaging subject area 1802 and the shared area C. Of these areas, the area overlapping the imaging subject area 1802 of the last time does not influence because the image information is already obtained by the previous imaging. On the other hand, in the shared area C, the ultrasonic beam is shielded on the imaging last time and also on the imaging this time, and so no image information has been obtained.

Next, the image analyzing means 1604 analyzes the ultrasonic image shown in FIG. 19, and detects the shielded area B as in the case of the shielded area A. At this time, the image analyzing means 1604 calculates the coordinate of a point of intersection Q of the boundary of the shielded area A and the boundary of the shielded area B, and outputs the image analysis results including this coordinate to the ultrasonic beam output direction controlling means 1607.

Figure 20:
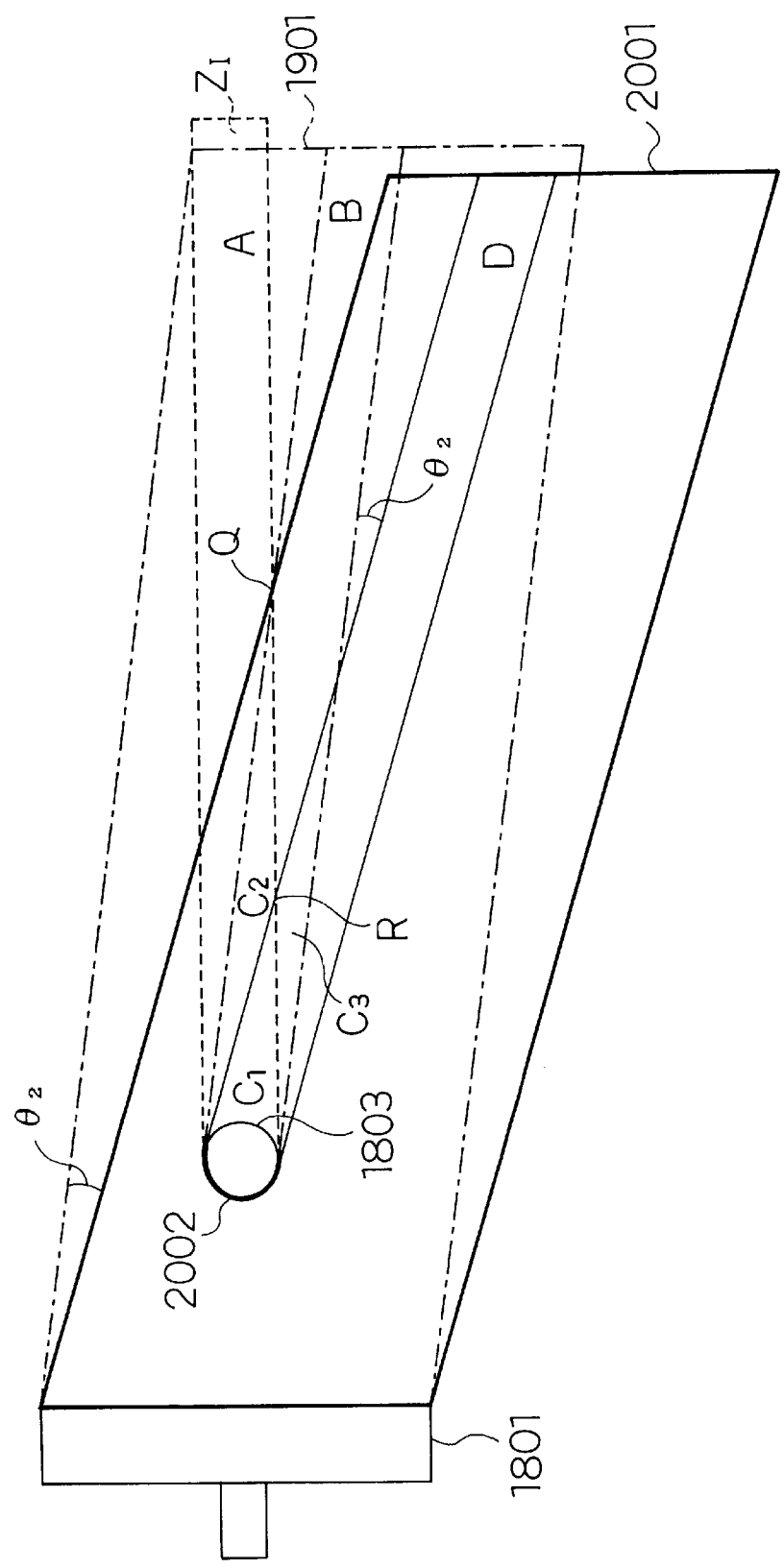
FIG. 20 is a diagram for explaining an operation of the ultrasonic image generating apparatus according to the first to third embodiment of the present invention.

On receiving the image analysis results, the ultrasonic beam output direction controlling means 1607 further changes the ultrasonic beam output angle of the ultrasonic beam output direction controlling means 1607 from $\theta_1$ based on this. As shown in FIG. 20, this change further rotates the outgoing angle of the ultrasonic beam by an angle $\theta_2$ so that the long side of a new imaging subject area 2001 passes through the point of intersection Q of the boundary of the shielded area A and the boundary of the shielded area B. Hereafter, the ultrasonic beam is outputted to be formed the new imaging subject area 2001 from the ultrasonic wave sending portion 1606 of the ultrasonic probe 1801, and the same image generating operation as in FIG. 18 is performed so that the ultrasonic image in the imaging subject area 2001 in FIG. 20 is obtained.

In the new imaging subject area 2001, the image information on the areas excluding a shielded area D is obtained. In addition, as the ultrasonic beam is inclined to the object 1803 by the angle $\theta_2$ from previous angle and strikes on a change face 2002, the newly formed shielded area D also intersects with the shielded area B at the angle $\theta_2$, and includes a shared areas $C_1$ and $C_3$ overlapping the shielded area B. At this time, the shared area $C_1$ is also overlapping the shielded area A.

The shared area C in the image last time is divided into the shared area $C_1$ and a small area $C_2$ by the boundary of the shielded area D. Of these areas, the small area $C_2$ is outside the shielded area D, and so it obtains the image information for the first time as the ultrasonic beam reaches and is reflected this time. On the other hand, the shared area $C_1$ is overlapping the shielded area D and the ultrasonic beam is shielded therefrom so that no image information has been obtained on the imaging even in this time. Moreover, the shared areas $C_3$ does not influence even if included in the shielded area this time since the image information has already been obtained on the imaging of the image in FIG. 18.

Next, the image analyzing means 1604 analyzes the ultrasonic image shown in FIG. 20, and detects the shielded area D as in the case of the shielded areas A and B. At this time, the image analyzing means 1604 calculates the coordinate of a point of intersection R of the boundary of the shielded area B and the boundary of the shielded area D, and outputs the image analysis results including this coordinate to the ultrasonic beam output direction controlling means 1607.

On receiving the image analysis results, the ultrasonic beam output direction controlling means 1607 further changes the ultrasonic beam output angle of the ultrasonic beam output direction controlling means 1607 based on the results. This change rotates the outgoing angle of the ultrasonic beam so that the long side of the new imaging subject area passes through the point of intersection R of the shielded area B and the shielded area D shown in FIG. 20.

Hereafter, the above series of operations are repeated, and the images are picked up while gradually rotating the outgoing angle of the ultrasonic beam according to the generation and analysis of the ultrasonic image. If all the information on the picked-up images is put together, the shielded areas are accumulated and reduced.

Figure 21:
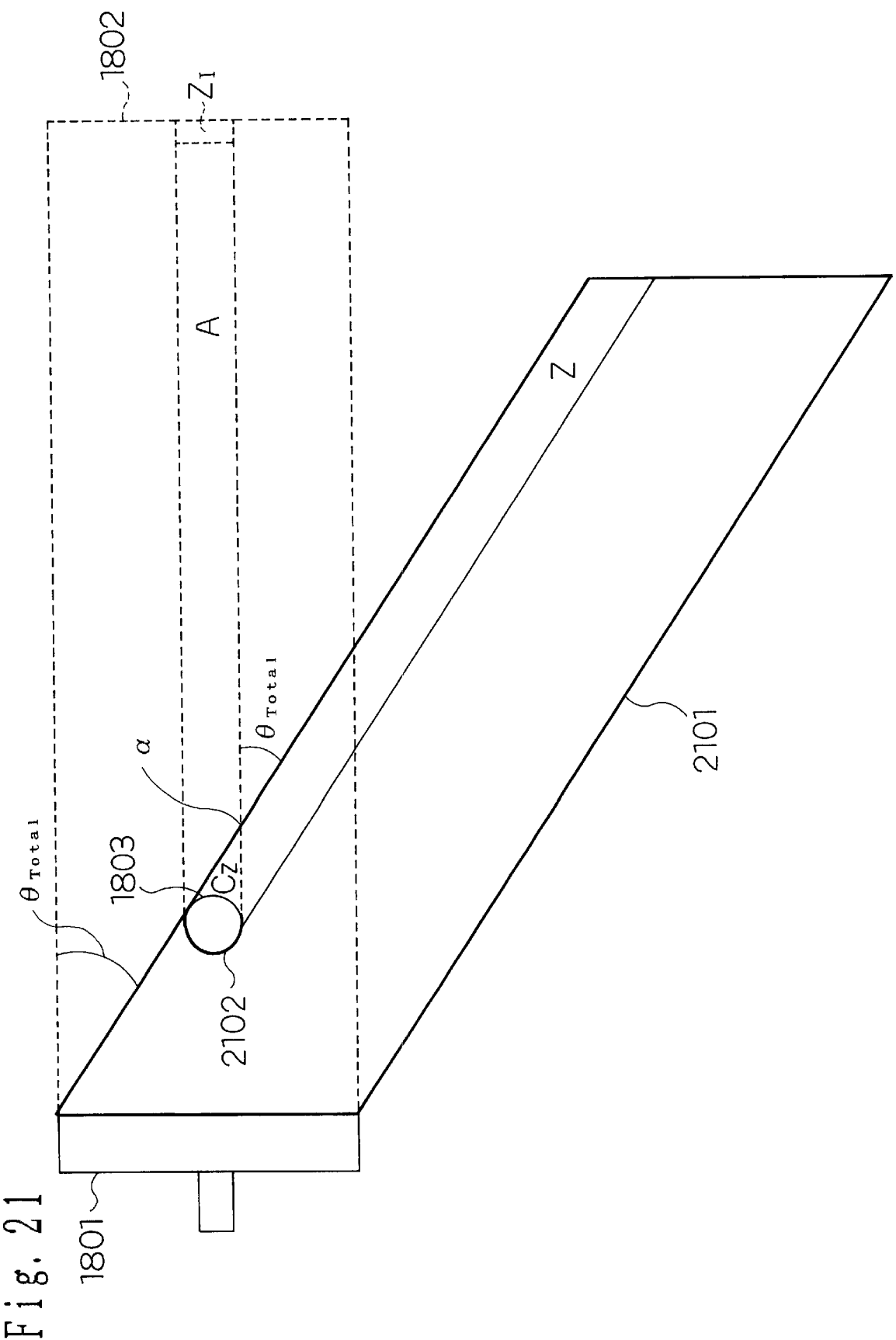
FIG. 21 is a diagram for explaining the operation of the ultrasonic image generating apparatus according to the first to third embodiment of the present invention.

Here, FIG. 21 shows the image of an imaging subject area 2101 when the outgoing angle of the ultrasonic beam is rotated to a critical angle $\theta_{total}$ (the angle where a new shielded area is no longer formed even if the outgoing angle is further rotated). In the drawing, as the ultrasonic beam is inclined to the object 1803 by the angle $\theta_{total}$ from the initial state and strikes on a change face 2102, a newly formed shielded area Z also intersects with the shielded area A at the angle $\theta_{total}$, and includes a critical shielded area $C_Z$ overlapping the shielded area A. The critical shielded area $C_Z$ has the ultrasonic beam shielded therefrom from the initial state and also on the imaging this time, and so it is left as the area where no image information is obtained as long as the outgoing direction is rotated in the critical angle direction.

Furthermore, the image analyzing means 1604 analyzes the ultrasonic image shown in FIG. 21, and detects the shielded area Z. At this time, the image analyzing means 1604 calculates the coordinate of the point of intersection α of the boundary of the shielded area A and the boundary of the shielded area Z, and outputs the image analysis results including this coordinate to the ultrasonic beam output direction controlling means 1607.

Figure 22:
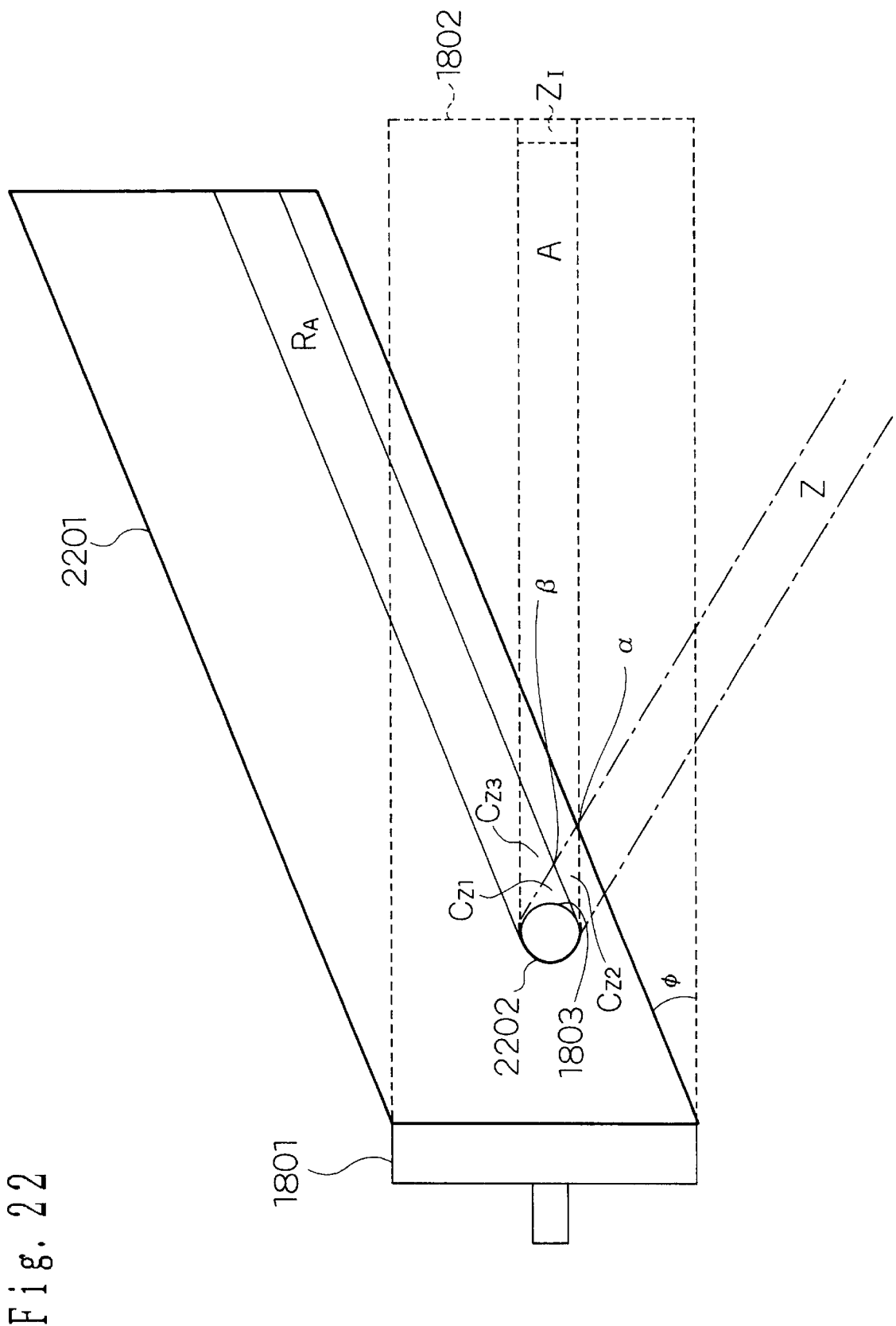
FIG. 22 is a diagram for explaining the operation of the ultrasonic image generating apparatus according to the first to third embodiment of the present invention.

On receiving the image analysis results, the ultrasonic beam output direction controlling means 1607 further changes the ultrasonic beam output angle of the ultrasonic beam output direction controlling means 1607 based on the results. As shown in FIG. 22, this change inversely rotates the outgoing angle of the ultrasonic beam by the angle $\phi$ from the initial state (by the angle $(\phi+\theta_{total})$ from the state shown in FIG. 21) so that the long side of the new imaging subject area passes through the point of intersection α.

The image picked up by this change means that the image information on the areas except a shielded area $R_A$ is obtained in an imaging subject area 2201 shown in FIG. 22. In addition, as the ultrasonic beam is inclined to the object 1803 in a reverse direction by the angle $\phi$ and strikes on a change face 2202, the newly formed shielded area $R_A$ also intersects with the shielded area A at the angle $\phi$, and includes shared areas $C_{Z1}$ and $C_{Z3}$ overlapping the shielded area A.

The shielded area Z in the image last time is divided into the shared area $C_{Z1}$ and a small area $C_{Z2}$ by the boundary of the shielded area $R_A$. Of these areas, the small area $C_{Z2}$ was included in the shielded area $C_Z$ but is outside the shielded area $R_A$ this time, and so it obtains the image information for the first time as the ultrasonic beam reaches and is reflected this time. On the other hand, the shared area $C_{Z1}$ is overlapping the shielded area $R_A$ and the ultrasonic beam is shielded therefrom so that no image information has been obtained on the imaging even in this time. Moreover, the shared areas $C_{Z3}$ does not influence even if included in the shielded area $R_A$ this time since the image information has already been obtained on the imaging of the images in FIGS. 19 to 21.

Furthermore, the image analyzing means 1604 analyzes the ultrasonic image shown in FIG. 22, and detects the shielded area $R_A$. At this time, the image analyzing means 1604 calculates the coordinate of a point of intersection β of the boundary of the shielded area Z and the boundary of the shielded area $R_A$, and outputs the image analysis results including this coordinate to the ultrasonic beam output direction controlling means 1607.

Hereafter, the same operation as that of obtaining the images of FIGS. 19 to 21 is performed so that an imaging operation is continued until reaching a critical angle in the angle $\phi$ direction.

While the images created by the image generating means 1603 have the shielded areas according to the forms of the objects 1803 respectively, the position of the shielded area is different in each image. Therefore, the information on the areas other than the shielded area overlapping and sharing in all the images is obtained. Therefore it is possible, by overlapping these images, to obtain the image information on the shielded area A in the initial state.

Figure 23:
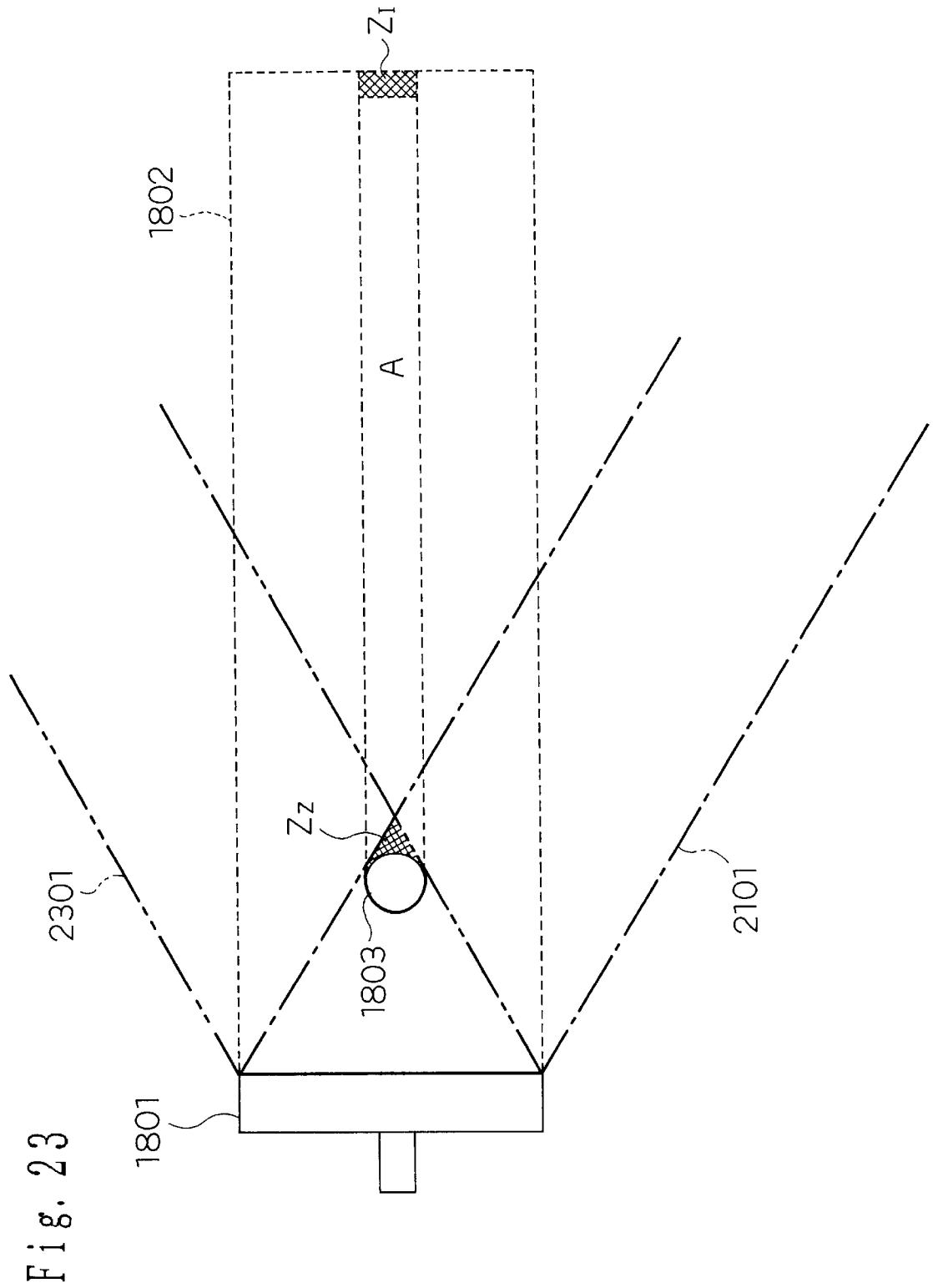
FIG. 23 is a diagram for explaining the operation of the ultrasonic image generating apparatus according to the first to third embodiment of the present invention.

FIG. 23 schematically shows a synthetic image obtained by synthesizing the images obtained by the above series of operations. While the image obtained by the imaging in the initial state included the shielded area A, the position of the shielded area A is detected and every time the imaging is repeated based on the position, the outgoing direction of the ultrasonic beam is rotated to the right and left critical angles (the drawing only shows the imaging subject area 2101 when at the right side critical angle seen from the outgoing direction of the ultrasonic beam and an imaging subject area 2301 when at the left side critical angle), and so it can be seen, in the synthetic image, that the images of most areas are obtained except a last shielded area $Z_Z$ in the area immediately behind the object 1803 and overlapping all the shielded areas in the shielded area A and an imaging incapable area $Z_I$ incapable of imaging from the beginning being outside the critical distance of the ultrasonic beam of which direction was changed. In this case, it is desirable to adjust the brightness and contrast of the images in advance for the sake of adjusting the image quality in the case of rendering them as one image.

Moreover, while the synthetic image in FIG. 23 was described as one still image, the ultrasonic image generating apparatus often displays the image as a dynamic image in fact. In this case, if the dynamic image is generated with the image of which outgoing direction of the ultrasonic beam is changed for each frame as mentioned above, the displayed dynamic image is substantially visible like the synthetic image. In general, since the number of frames per one second which can be generated by the ultrasonic image generating apparatus is 100 fps or less and 80 to 90 fps or so, it is possible to pick up and display the images of which angle is changed from the initial state to the right and left critical angles at least within one second so that human eyes perceive them in a substantially overlapping state. Therefore, the operation of creating the synthetic image may be omitted.

In addition, it is not necessary to perform the operation of the image analysis and change of the outgoing direction by the image analyzing means 1604 for each time that one image is generated, but it may be performed for each time that a predetermined number of images are generated. In this case, a plurality of images having the same outgoing direction of the ultrasonic beam are obtained so that, in the case of obtaining the dynamic image by using this image as the frame, the position of the shielded area gradually rotates from the initial state like animation and the inside of the shielded area A in the initial state is gradually displayed. In this case, the number of frames to be generated is 60 fps or 30 fps so as to constitute some in the frames with the images generated in the same direction.

In addition, in the above operation of detecting the brightness, as in the case of determining the critical distance, the first and second reference values should be set by picking up in advance the object having the known hardness and size and caliculating the difference between the brightness thereof and the brightness of the portion surrounding the imaging position. Moreover, in the case where the analysis by the image analyzing means 1604 has some problems, the parameters of the first and second reference values should be changed by the condition setting means 1608.

(Second Embodiment)

Figure 24:
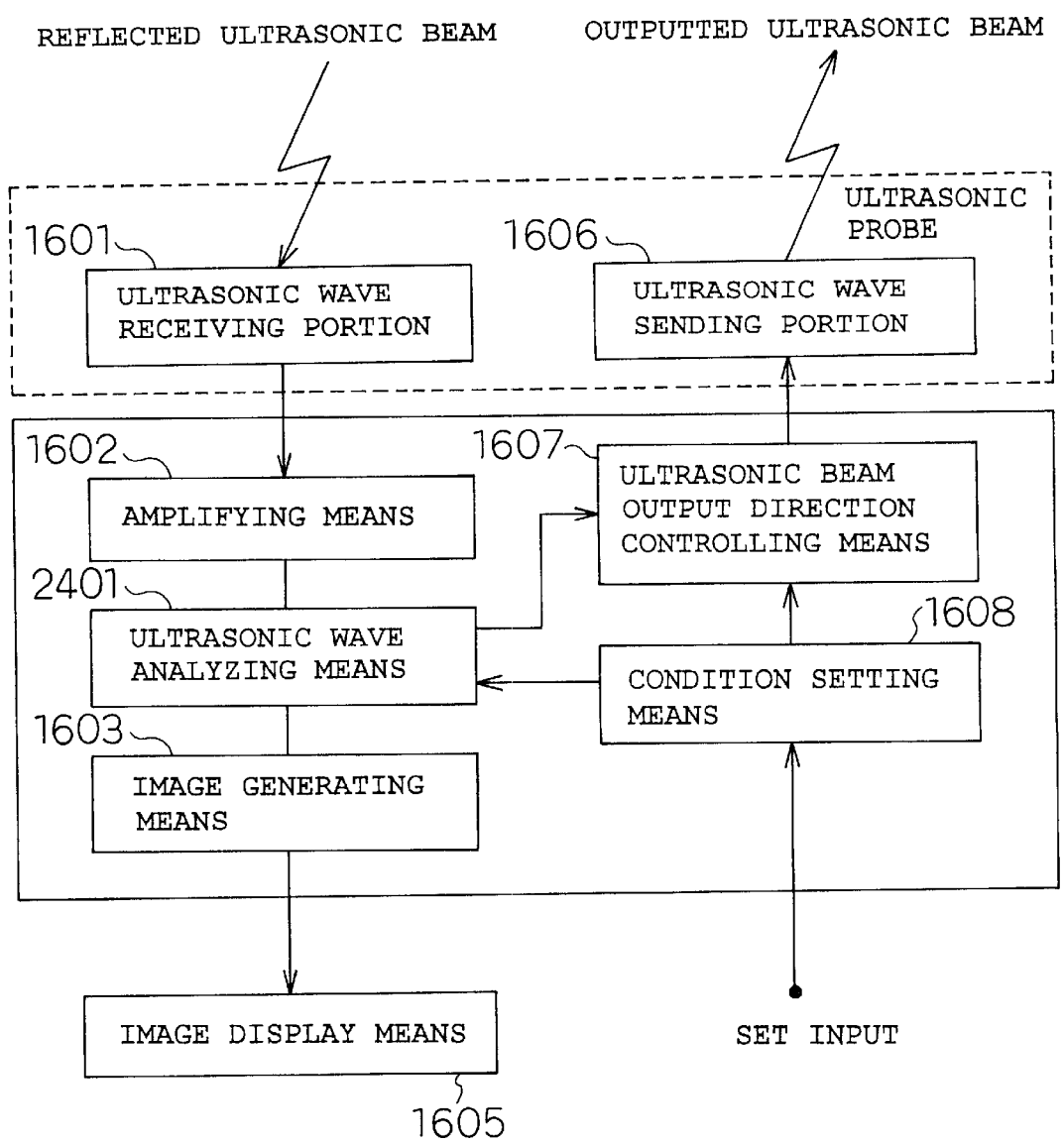
FIG. 24 is a block diagram showing a configuration of the ultrasonic image generating apparatus according to a second embodiment of the present invention.

FIG. 24 shows a schematic block diagram of the ultrasonic image generating apparatus according to a second embodiment of the present invention. The portions which are the same as or equivalent to those in FIG. 16 are given the same reference numerals, and detailed description thereof will be omitted. An ultrasonic image generating apparatus 2400 according to this embodiment is different in that the image analyzing means 1604 is omitted, and an ultrasonic wave analyzing means 2401 is provided between the amplifying means 1602 and image generating means 1603, and the ultrasonic beam output direction controlling means 1607 controls the direction of the ultrasonic beam outputted by the ultrasonic wave sending portion 1606 based on the analysis results of the ultrasonic wave analyzing means 2401.

Hereafter, the operation of the ultrasonic image generating apparatus according to the second embodiment of the present invention will be described, and an embodiment of the ultrasonic image generating method of the present invention will also be described thereby. However, the same points as in the first embodiment will be omitted, and the differences will be mainly described.

In the case where there is the object in the imaging subject area, the ultrasonic beam emitted in the same initial state as in the first embodiment is reflected on it and is received as the reflected ultrasonic beam by the ultrasonic wave receiving portion 1601. The received reflected ultrasonic beam is sent as the ultrasonic wave data to the amplifying means 1602, where it is amplified and then inputted to an ultrasonic wave analyzing means 2401.

As in the first embodiment, if an imaging object 1803 having sufficient hardness and totally reflecting a hit ultrasonic wave in substance is in the imaging subject area 1802, the ultrasonic beam is shielded and a shielded area A is formed in the rear of the object 1803 seen from the ultrasonic probe 1801, and the other areas are shown to be visible as the image information having at least the brightness of the critical distance or higher, because the areas include the information on the object reflecting only a part of the ultrasonic beam struck a change face 1804 and irregular reflection of the internal organization.

On the other hand, the ultrasonic wave analyzing means 2401 directly analyzes the ultrasonic wave data before the ultrasonic image shown in FIG. 18 is generated so as to detect the shielded area A. The detection is performed as follows.

On scanning of the ultrasonic beam, the ultrasonic wave analyzing means 2401 measures the intensity of the reflected ultrasonic beam as to the one-dimensional data constituting the long side of the imaging subject area 1802, and in the case where there is a portion of the brightness equal to or less than that of the critical distance, it is detected as a non-detected area in which no reflected ultrasonic beam is detected. As for the critical distance here, a reflector placed at a predetermined distance and having a known composition is picked up in advance by the ultrasonic beam so that the critical distance should be set based on the intensity of the reflected ultrasonic beam from the reflector. In addition, in the case of using the human body as the test object, it is desirable to use a body part in the proximity of the body part to be the imaging subject area 1802 and of which information on the inside is known in advance. For instance, in the case where the length of the depth is known in advance and placement of the internal organization is also known in advance, the critical distance should be determined based on the intensity of the reflected ultrasonic beam in the depth.

The ultrasonic wave analyzing means 2401 rearranges one-dimensional ultrasonic wave data according to the scan, detects the set as the non-detected area in the case where a non-detected portion is extended like a two-dimensional plane, and outputs it together with coordinate information defining it to the ultrasonic beam output direction controlling means 1607.

On obtaining the analysis results, the ultrasonic beam output direction controlling means 1607 changes the ultrasonic beam output direction of the ultrasonic beam output direction controlling means 1607 from the initial state based on the results. The operations of changing the ultrasonic beam output direction and generating the image are performed as in the first embodiment except a step of generating the data to be a source of the control of the ultrasonic beam output direction controlling means 1607 so that the images shown in FIGS. 19 to 23 can be obtained. As for display of the images, it should be performed as in the first embodiment.

Moreover, in the case where it is determined, from the image generated by image generating means 1605, the analysis by the ultrasonic wave analyzing means 2401 have some problems, the parameters of the brightness of giving the critical distance and non-detected areas should be changed from the condition setting means 1608.

In addition, while it was described, in the above first and second embodiments, that the ultrasonic beam output direction controlling means 1607 changes the ultrasonic beam outgoing direction to the critical angle, it may also be set to stop the control at an arbitrary direction less than the critical angle by the condition setting means 1608.

(Third Embodiment)

Figure 25:
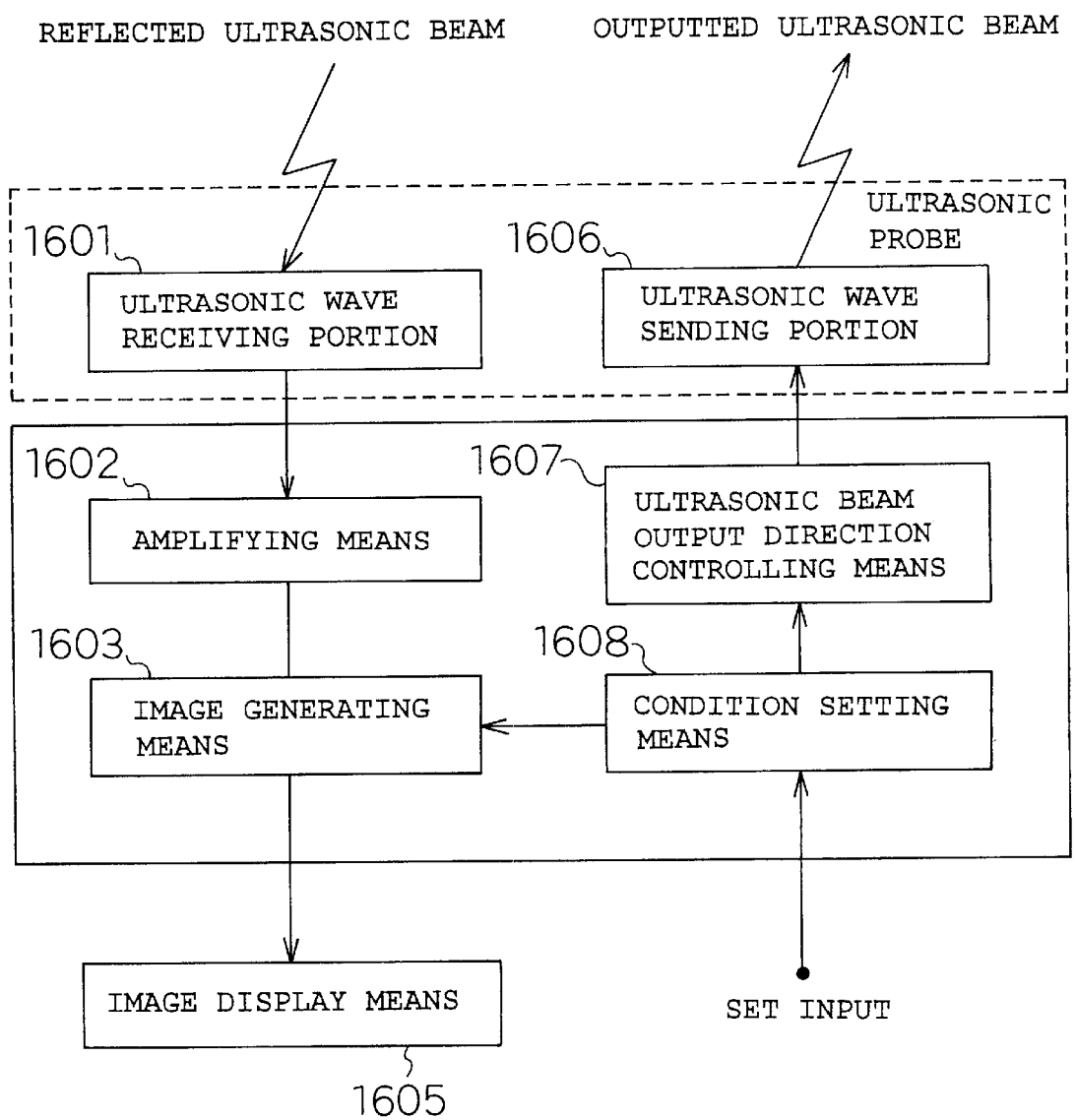
FIG. 25 is a block diagram showing the configuration of the image generating means of the ultrasonic image generating apparatus according to a third embodiment of the present invention.

FIG. 25 shows a schematic block diagram of the ultrasonic image generating apparatus according to a third embodiment of the present invention. The portions which are the same as or equivalent to those in FIG. 16 are given the same reference numerals, and detailed description thereof will be omitted. An ultrasonic image generating apparatus 2500 according to this embodiment is different in that the image analyzing means 1604 is omitted, and the ultrasonic beam output direction controlling means 1607 controls the direction of the ultrasonic beam outputted by the ultrasonic wave sending portion 1606 without any kinds of feed back operation based on the set input from the condition setting means 1608.

Hereafter, the operation of the ultrasonic image generating apparatus according to the third embodiment of the present invention having such a configuration will be described, and an embodiment of the ultrasonic image generating method of the present invention will also be described thereby. However, the same points as in the first embodiment will be omitted, and the differences will be mainly described.

First of all, the user determines the direction of the ultrasonic probe 1801 to a desired imaging subject area as the initial state, and fixes the probe so that it will not move, and also sets the ultrasonic beam outgoing direction of the ultrasonic beam output direction controlling means 1607 in one predetermined direction. Next, the ultrasonic beam is outputted to the imaging area from the ultrasonic wave sending portion 1606 of the ultrasonic probe 1801. In the case where there is the object in the imaging subject area, the ultrasonic beam reflected on it is received as the reflected ultrasonic beam by the ultrasonic wave receiving portion 1601. The received reflected ultrasonic beam is sent as the ultrasonic wave data to the amplifying means 1602, where it is amplified and then inputted to the image generating means 1603. In the image generating means 1603, the image generating arithmetic section 1701 sequentially accumulates the amplified ultrasonic wave data and rearranges it in a two-dimensional array so as to generate the image. The generated image is sent to the frame memory 1702. The image stored in the frame memory 1702 is outputted to the image displaying means 1604.

At this time, the ultrasonic beam output direction controlling means 1607 electrically, that is automatically changes the outgoing direction of the ultrasonic beam based on the setting of the condition setting means 1608 irrespective of the state of the picked-up image. While the parameters such as the outgoing direction and a period of the change may be arbitrary, it is also feasible that the user refers to the image picked up in the initial state and make a correction as appropriate based on it from the condition setting means 1608.

It is possible, by having such a configuration, to implement the changes in the imaging position similar to the examples shown in FIGS. 18 to 23 and obtain in the imaging subject area the ultrasonic image wherein the area in which the ultrasonic beam is shielded by the imaging object is reduced in advance.

In addition, as this embodiment omits the image analysis or ultrasonic beam analysis, it also has an effect of omitting the time required for the analysis and providing the image easy to follow real-time animation display.

Moreover, while the above first to third embodiments are described and shown in the drawings on the assumption that the imaging subject area is a rectangle or a parallelogram, the imaging subject area may also be another shape such as an ellipse or a fan shape, provided that the shape should include the critical distance as its parameter.

Moreover, in the above first to third embodiments, the ultrasonic wave receiving portion 1601 is equivalent to the ultrasonic beam receiving means of the present invention, and the image generating means 1603 is equivalent to the image generating means thereof. In addition, the ultrasonic wave sending portion 1606 is equivalent to the ultrasonic beam outputting means of the present invention, and the ultrasonic beam output direction controlling means 1607 is equivalent to the ultrasonic beam output direction controlling means thereof. In addition, image analyzing means 1604 is equivalent to the image analyzing means of the present invention, and the ultrasonic wave analyzing means 2401 is equivalent to the reflected ultrasonic beam analyzing means thereof. Therefore, it is also possible to have the configuration wherein the amplifying means 1602 and the condition setting means 1608 are omitted from the above embodiments.

In addition, the program according to the present invention may be the program of having the functions of all or a part of means of the above-mentioned ultrasonic image generating apparatus of the present invention executed by the computer, which may be the program of operating in synergy with the computer.

In addition, the present invention maybe a medium having the program of having the functions of all or a part of means of the above-mentioned ultrasonic image generating apparatus of the present invention executed by the computer, which may be the medium wherein the above described program readable and read by the computer performs the above described functions in synergy with the above described computer.

Moreover, the above "a part of means (or apparatuses, elements, circuits, portions and so on)" of the present invention and the above "a part of the steps (or processes, operations, actions and so on)" thereof refer to a few means or steps of the plurality of means or steps, or refer to a certain function or a certain operation in one means or step.

In addition, a part of the apparatuses (or elements, circuits, portions and so on) of the present invention refer to a few apparatuses of the plurality of the apparatuses, or refer to a certain means (or elements, circuits, portions and so on) in one apparatus, or refer to a certain function in one means.

In addition, a record medium having recorded the program of the present invention and readable by the computer is also included in the present invention.

In addition, one form of using the program of the present invention may be an aspect wherein it is recorded in the record medium readable by the computer and operates in synergy with the computer.

In addition, one form of using the program of the present invention may be an aspect wherein it is transmitted in a transmission medium, read by the computer and operates in synergy with the computer.

In addition, data structure of the present invention includes a database, a data format, a data table, a data list, a data type and so on.

In addition, the record media include a ROM and so on, and the transmission media include transmission mechanisms such as the Internet, light, radio wave, sound wave and so on.

In addition, the above-mentioned computer of the present invention is not limited to sheer hardware such as a CPU but may also include firmware, an OS and even peripherals.

Moreover, as described above, the configuration of the present invention may be implemented either as software or as hardware.

(Fourth Embodiment)

FIG. 1 shows a schematic block diagram of the ultrasonic image generating apparatus according to a fourth embodiment of the invention described later. Hereafter, the configuration and operation thereof will be described.

An ultrasonic sensor 101 receives sound, and an amplifying means 102 is an amplifier wherein signal processing for general image composition is performed. An image generating means 103 generates the image from the sound information, and writes the image data to the storage device such as the frame memory. Image measuring means 104 is means of measuring a brightness value for a generated image. Index calculating means 107 receives the brightness value measured by the image measuring means 104, and calculates the sum and average thereof as image indexes and sends them to amplification factor controlling means 105. The amplification factor controlling means 105 controls an amplification factor of a received signal based on the image indexes. Image display means 106 displays the image data in the image generating means 103.

Figure 2:
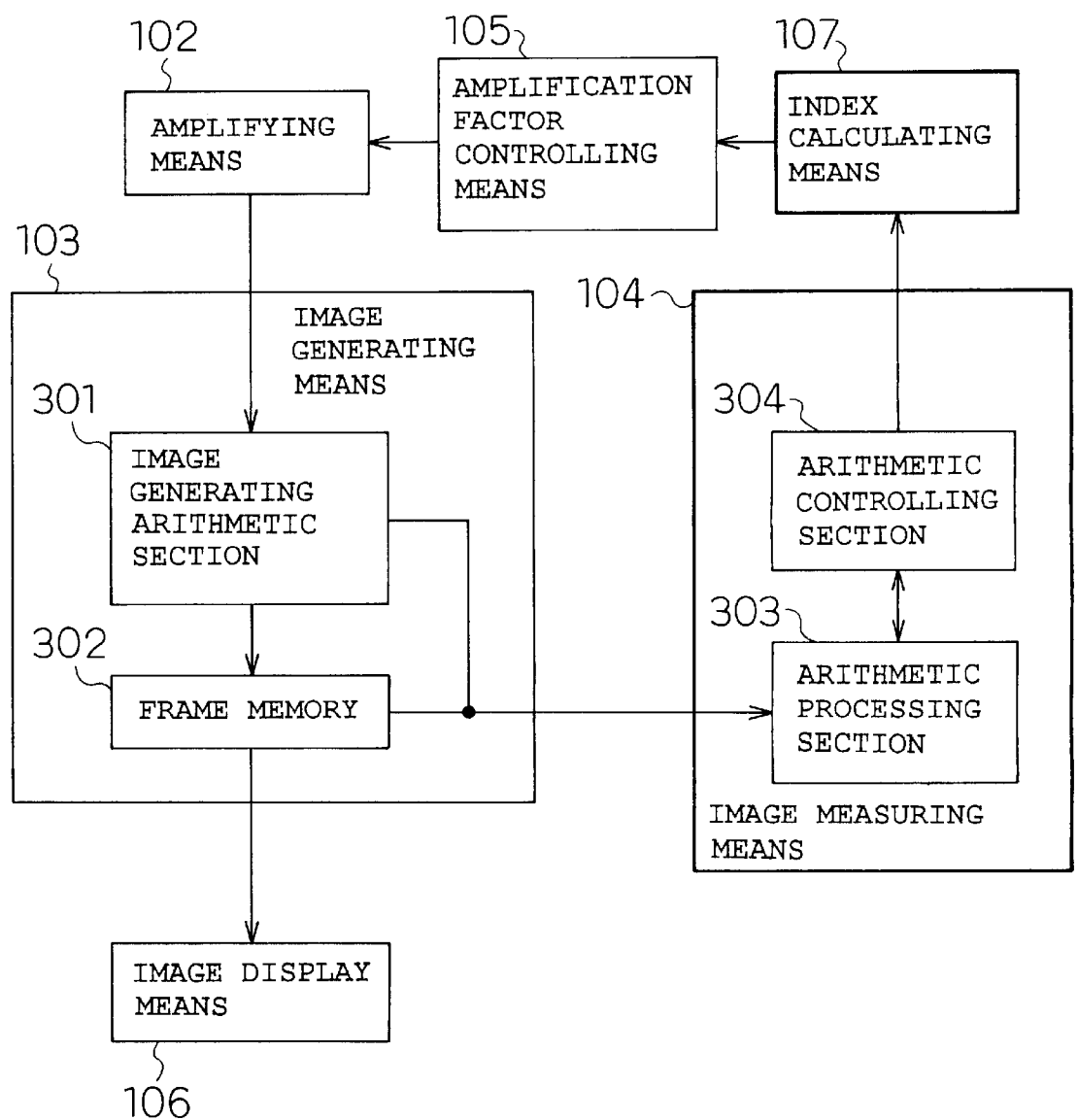
FIG. 2 is a block diagram showing internal configurations of image generating means 103 and image measuring means 104.

Next, FIG. 2 is a block diagram showing internal configurations of the image generating means 103 and image measuring means 104 of the ultrasonic image generating apparatus. In FIG. 2, the portions which are the same as or equivalent to those in FIG. 1 are given the same reference numerals, and detailed description thereof will be omitted.

The image generating means 103 is comprised of an image generating arithmetic section 301 of collecting a plurality of pieces of sound data which is one-dimensional data and arranging them in a predetermined order to generate two-dimensional data, and a frame memory 302 of holding the generated image data. In the image generating arithmetic section 301, rearrangement of the collected plurality of pieces of sound data and interpolating calculation in conjunction therewith are performed.

The image measuring means 104 is comprised of an arithmetic processing section 303 equivalent to a general CPU, DSP or the like and an arithmetic controlling section 304 of controlling it.

The arithmetic processing section 303 measures the brightness value of the image data, and sends the measurement result to the arithmetic controlling section 304. The image data is obtained from the image generating arithmetic section 301 or the frame memory 302. The arithmetic controlling section 304 processes the image area to be calculated and the measurement result thereof, and sends them to the index calculating means 107.

A sound signal transmitted as a reflected wave from the object not shown and received by the ultrasonic sensor 101 is sent to the amplifying means 102, and is amplified by the amplifying means 102 and then inputted to the image generating means 103. In the image generating means 103, the image generating arithmetic section 301 sequentially accumulates the amplified sound data and rearranges it in a two-dimensional array so as to generate the image. The generated image is sent to the frame memory 302 in order to output it to the image display means 106.

Figure 3:
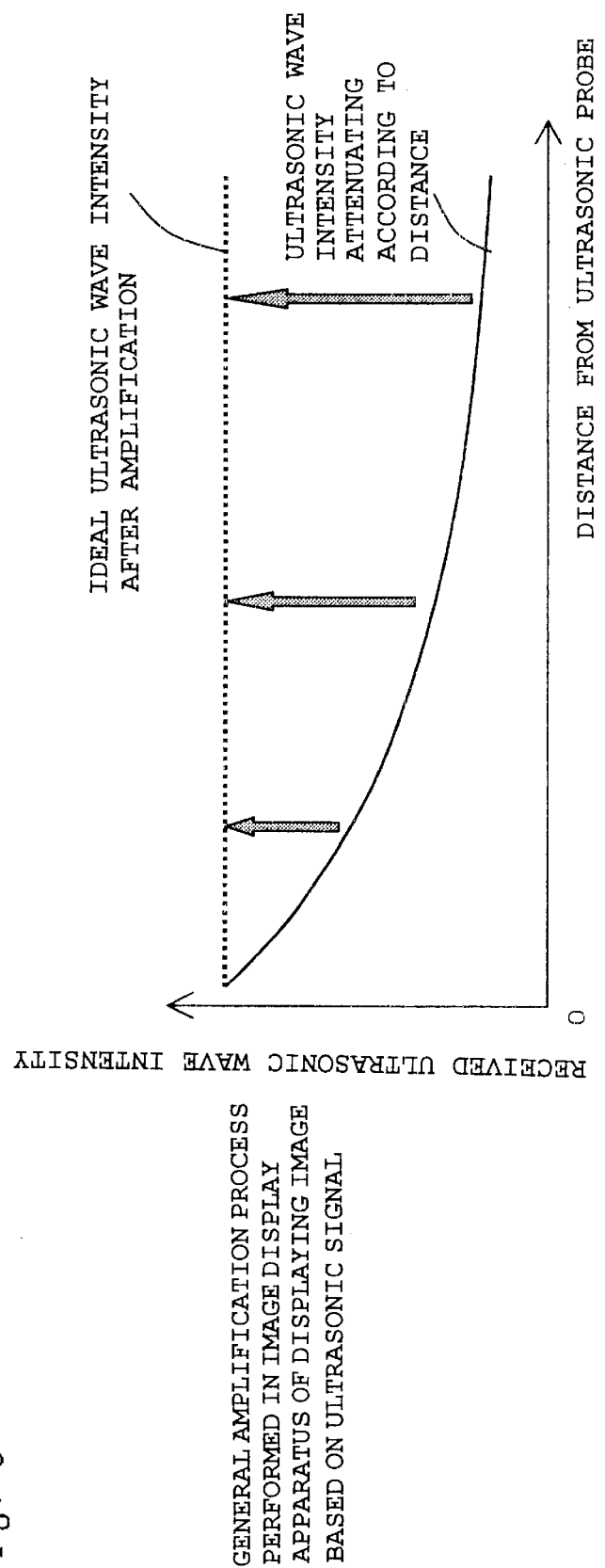
FIG. 3 is a diagram showing an amplification process performed in the ultrasonic image generating apparatus.

FIG. 3 is a diagram explaining an amplification process in the amplifying means 102. As for an ultrasonic signal, the larger the distance from the ultrasonic sensor 101 to the object which is a wave source is, the higher the attenuation becomes, and so it is amplified at a high amplification factor according to the distance from the ultrasonic sensor 101. As a result of such an amplification process, the ultrasonic signal of a fixed intensity is obtained irrespective of the distance from the ultrasonic sensor 101 to the object.

Incidentally, in case of using the ultrasonic sensor for a medical examination, it may happen that the attenuation of the ultrasonic signal becomes high for a reason other than the distance from the wave source of the reflected wave to the ultrasonic sensor 101, that is, due to significant sebum thickness of physical organization for instance.

Figure 4:
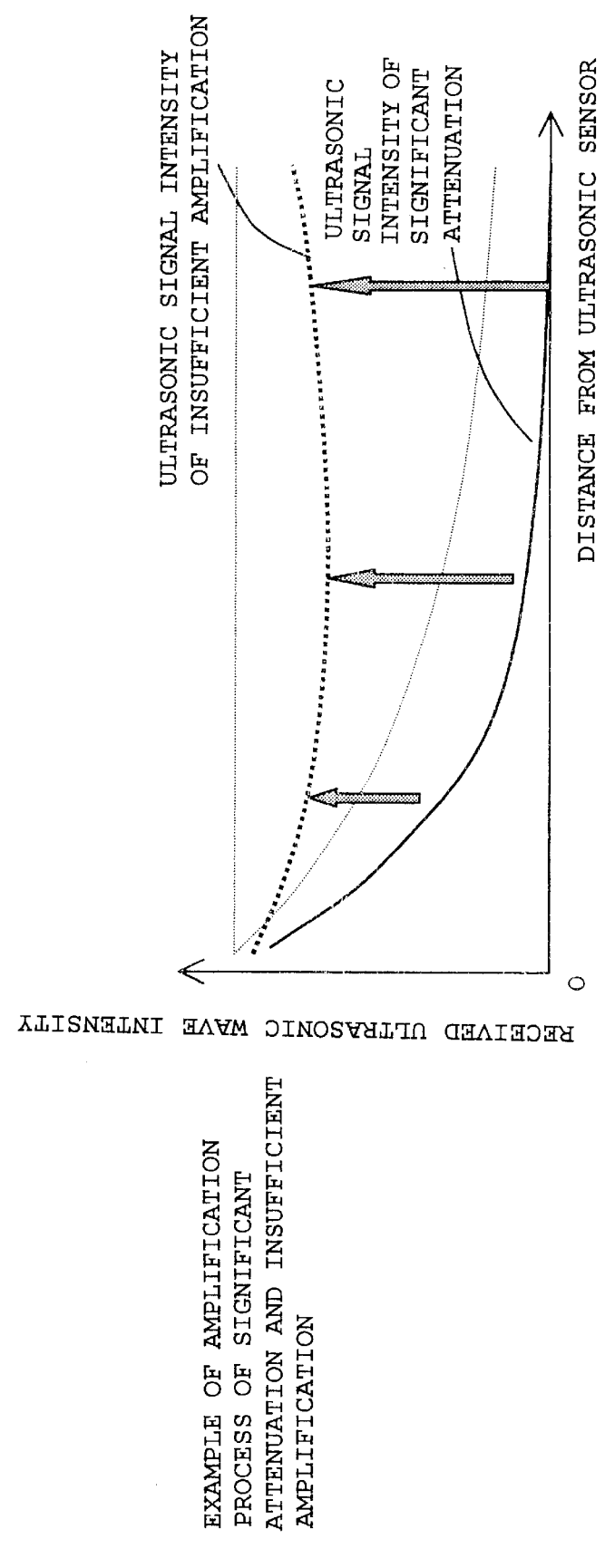
FIG. 4 is a diagram showing a state of insufficient signal intensity in the case of significant attenuation of an ultrasonic wave.

At this time, if the process of simply controlling the amplification factor of the amplification factor controlling means 105 according to the distance from the ultrasonic sensor 101 is performed as in FIG. 3, the state becomes as shown in FIG. 4, wherein the intensity of the sound signal after the amplification no longer corresponds fixedly to a depth direction of the physical organization which is the direction of propagation of the ultrasonic.

To solve this problem, in this embodiment, the image measuring means 104 measures the brightness value of the image data in the image generating means 103, the index calculating means 107 generates an image index based on the measured brightness value and feeds back brightness of the displayed image to the image generating means 103 so as to automatically perform STC and gain adjustment which were manually performed in the past.

A method of image adjustment by the index calculating means 107 by using the sum or average of the brightness values as an image index will be now described.

Figure 5A:
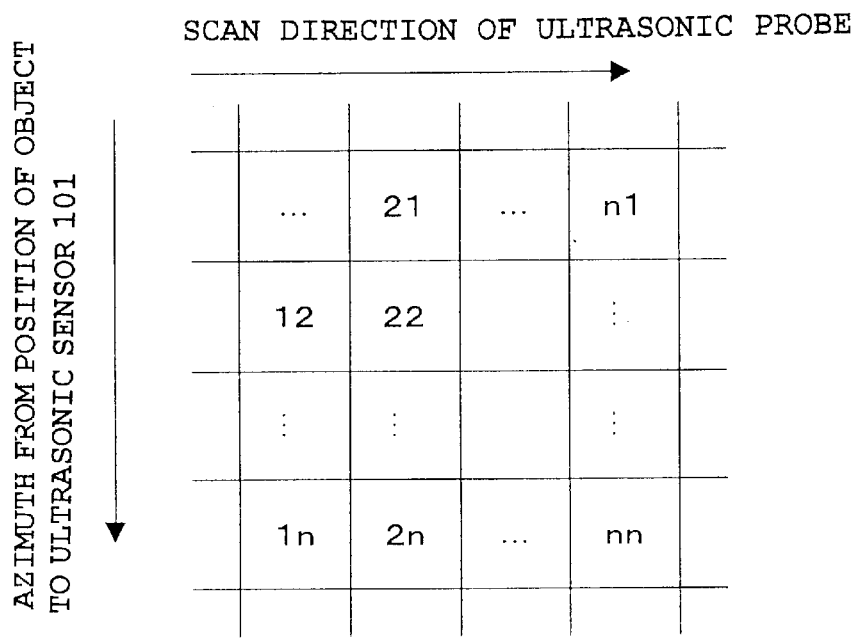
FIG. 5A is a diagram for explaining a method of image adjustment by an index calculating means 107 of using the sum or average of brightness values as an image index in the ultrasonic image generating apparatus according to the fourth embodiment.

As shown in FIG. 5A, in the image adjustment by using the sum and average of the brightness values, the image data is divided into rectangular small areas of a fixed size, and the sum or average of the brightness values is calculated for each of the small areas. The small areas may be set one-dimensionally in an azimuth from the position of the object to the ultrasonic sensor 101 or in a scan direction of the ultrasonic sensor, or they may also be set two-dimensionally both in the azimuth from the position of the object to the ultrasonic sensor 101 and in the scan direction of the ultrasonic sensor.

Next, it is examined, as to each area number assigned to the areas, whether or not variations in the calculated sums or averages are the predetermined value or more.

Figure 5B:
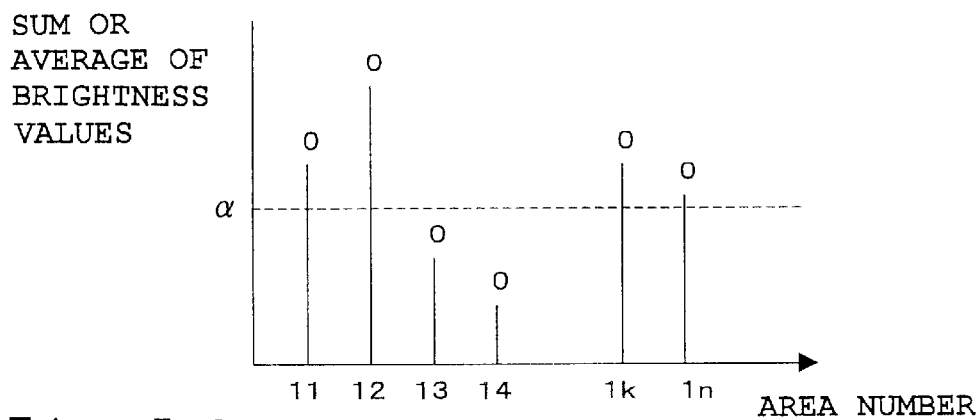
FIG. 5B is a diagram for explaining the method of image adjustment by the index calculating means 107 of using the sum or average of the brightness values as the image index in the ultrasonic image generating apparatus according to the fourth embodiment.
Figure 5C:
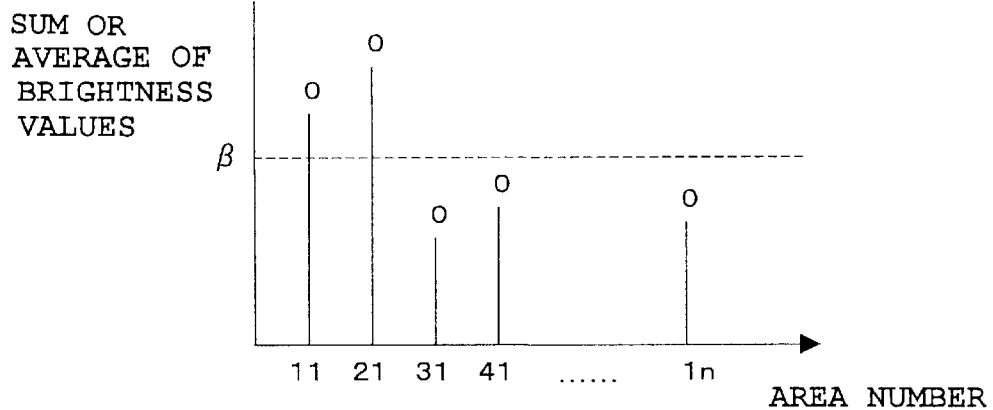
FIG. 5C is a diagram for explaining the method of image adjustment by the index calculating means 107 of using the sum or average of the brightness values as the image index in the ultrasonic image generating apparatus according to the fourth embodiment.

Here, FIGS. 5B and 5C show examples of correspondence of the sum or average of the brightness values as to each area number.

The example shown in FIG. 5B is a graph showing the correspondence of the sum or average of the brightness values as to each small area in the azimuth from the position of the object to the ultrasonic sensor 101, where an inspection object is supposedly depicted with sufficient brightness in the case of being equal to or exceeding the predetermined value α as with the area numbers 11 and 12 in the drawing.

On the other hand, in case of being less than the predetermined value, it is considered that sufficient brightness for depicting the inspection object has not been obtained, determining that the amplification in that azimuth is not appropriate. In the case of the values less than the predetermined value α as in the areas 13 and 14 in FIG. 5B, the amplification in that azimuth from the ultrasonic probe is not appropriate. In this case, the sufficient brightness can be obtained by increasing the amplification factors at the distance and scan position corresponding to the area numbers 13 and 14 respectively. On the other hand, the area number 1k indicates a position more distant from the position of the object than the area numbers 13 and 14, but the amplification factor is not changed since the brightness thereof has a value higher than the predetermined value α.

Next, the example shown in FIG. 5C is a graph showing the correspondence of the sum or average of the brightness values as to each small area in the scan direction of the ultrasonic sensor, where the inspection object is supposedly depicted with sufficient brightness in case of being equal to or exceeding the predetermined value β as with the area numbers 11 and 21 in the drawing.

On the other hand, in case of being less than the predetermined value, it is considered that there exists the object hardly passing the ultrasonic signal, or inversely, there does not exist the object itself.

In the former case, it is possible, by increasing the amplification factor of the distance and scan position corresponding to the area, to clearly display the image of the darkly depicted object. In this case, there is a brightly depicted portion in the area (that is, there is a portion strongly reflecting the ultrasonic wave) close to the ultrasonic probe rather than the currently dark area on the same sound ray, and so it is processed by rendering this relationship as a sign.

In the latter case, no amplification process is performed since there is no boundary of acoustic impedance of reflecting the ultrasonic wave and it can be determined to be a uniform substance. This determination is possible by concurrently using statistical indicators such as standard deviation and variance described later.

Figure 15A:
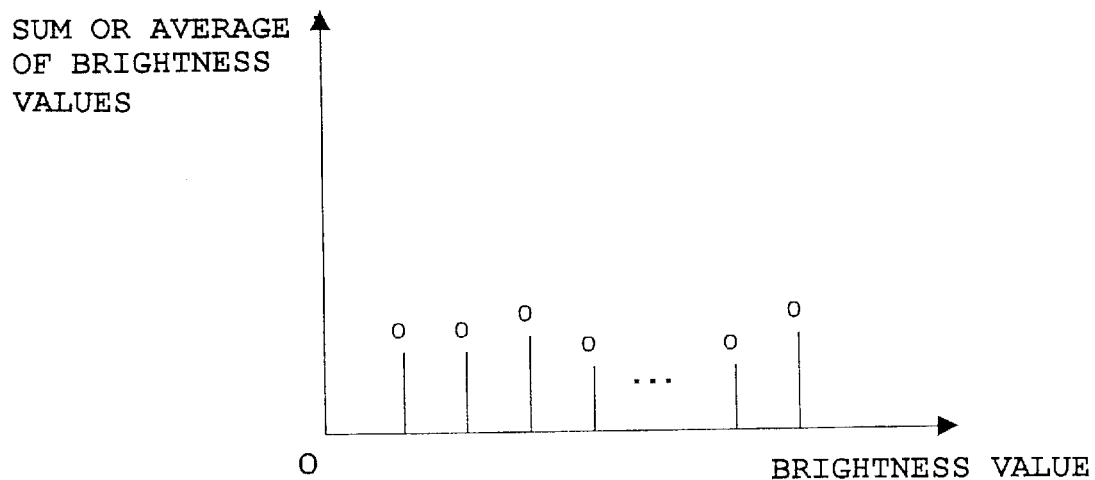
FIG. 15A is a diagram for explaining the method of image adjustment by the index calculating means 107 of using the sum or average of the brightness values as the image index in the ultrasonic image generating apparatus according to the fourth embodiment.

On the other hand, if the amplification factor is controlled simply by setting a threshold such as the above α or β, the entire screen is displayed almost at the same brightness as to each area as shown in FIG. 15A so that there is a possibility of becoming the image of little contrast.

Figure 15B:
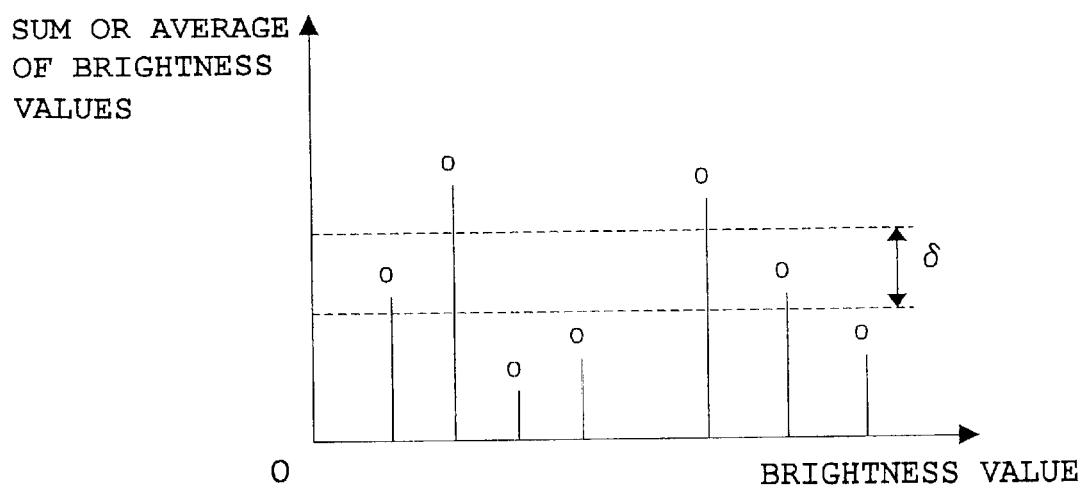
FIG. 15B is a diagram for explaining the method of image adjustment by the index calculating means 107 of using the sum or average of the brightness values as the image index in the ultrasonic image generating apparatus according to the fourth embodiment.

According to this embodiment, to prevent such a problem, the amplification factor is controlled by setting a predetermined range δ of the area so as to prevent the number of the areas of the sum or average of the pixel values of each area from centering on the range δ (not including the area of the predetermined number or more, and distributing to the values over and below that range). FIG. 15B is an example of performing this control. As shown in the drawing, in the case where some are deviating from the range δ even if the predetermined value α is reached as to the sum or average of the brightness values of each area, the entire screen is displayed with different brightness distribution so that the image has the contrast.

Here, FIG. 6 shows a sound wave intensity ideally amplified according to this embodiment and the sound wave intensity amplified according to the distance from the ultrasonic sensor 101 to the object. As shown in the drawing, in the case of this embodiment, it is possible to have the intensity of the sound signal after the amplification correspond fixedly to the depth direction of the physical organization which is the direction of propagation of the ultrasonic.

Moreover, while the amplification factor of the area below the predetermined value α or β is increased in the above description, it is also feasible to reduce the amplification factor of the areas other than the area below the predetermined value α or β. In this case, the brightness can be rendered uniform even though the entire brightness is reduced.

(Fifth Embodiment)

Figure 7:
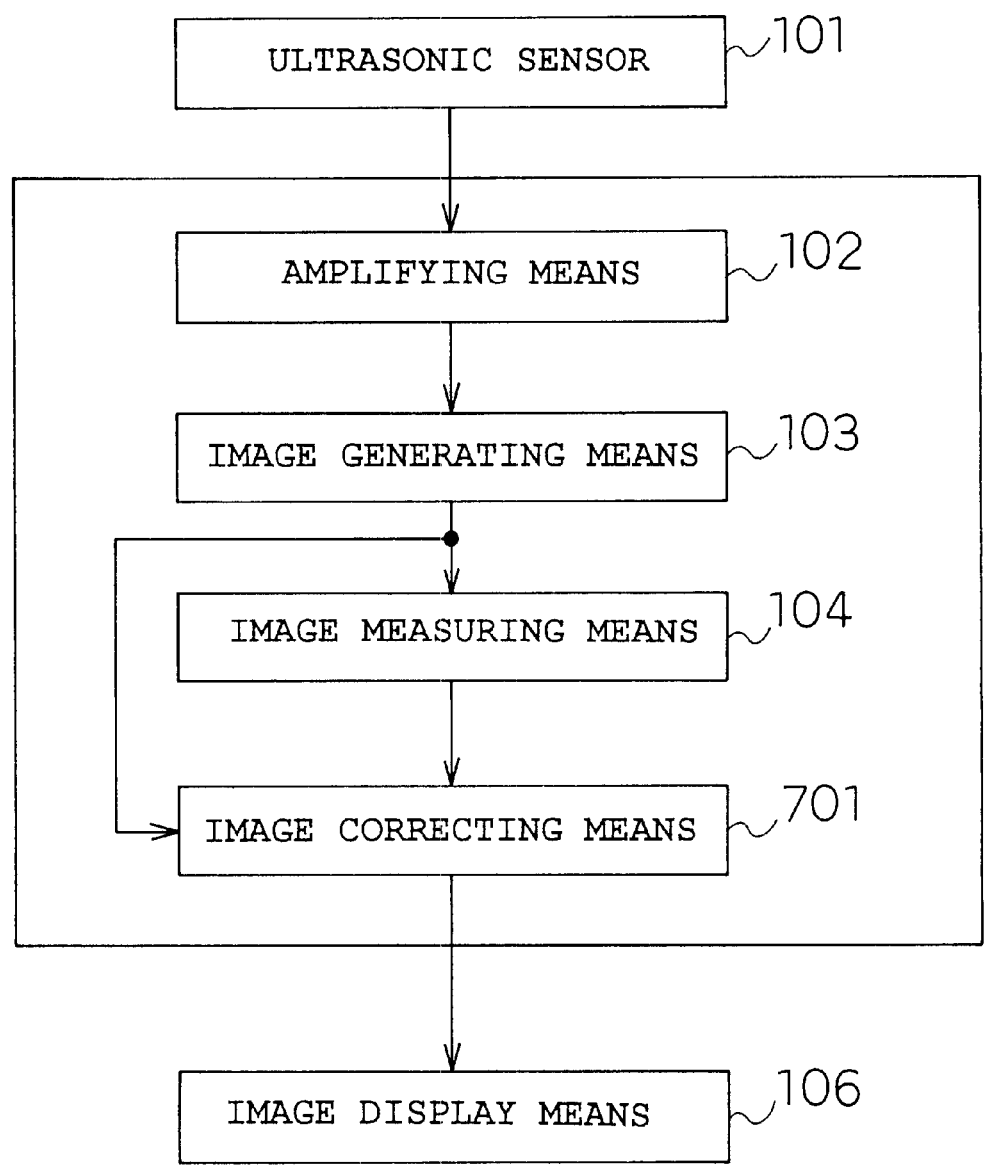
FIG. 7 is a block diagram showing a configuration of the ultrasonic image generating apparatus according to a fifth embodiment of the present invention.

FIG. 7 shows a schematic block diagram of the ultrasonic image generating apparatus according to a fifth embodiment of the invention. Hereafter, the configuration and operation thereof will be described.

In the drawing, the portions which are the same as or equivalent to those in FIG. 1 are given the same reference numerals, and detailed description thereof will be omitted. In addition, image correcting means 701 receives the brightness value measured by the image measuring means 104 and creates a histogram corresponding thereto, and corrects the image by using the variance and standard deviation of the brightness value as the image indexes.

Figure 8:
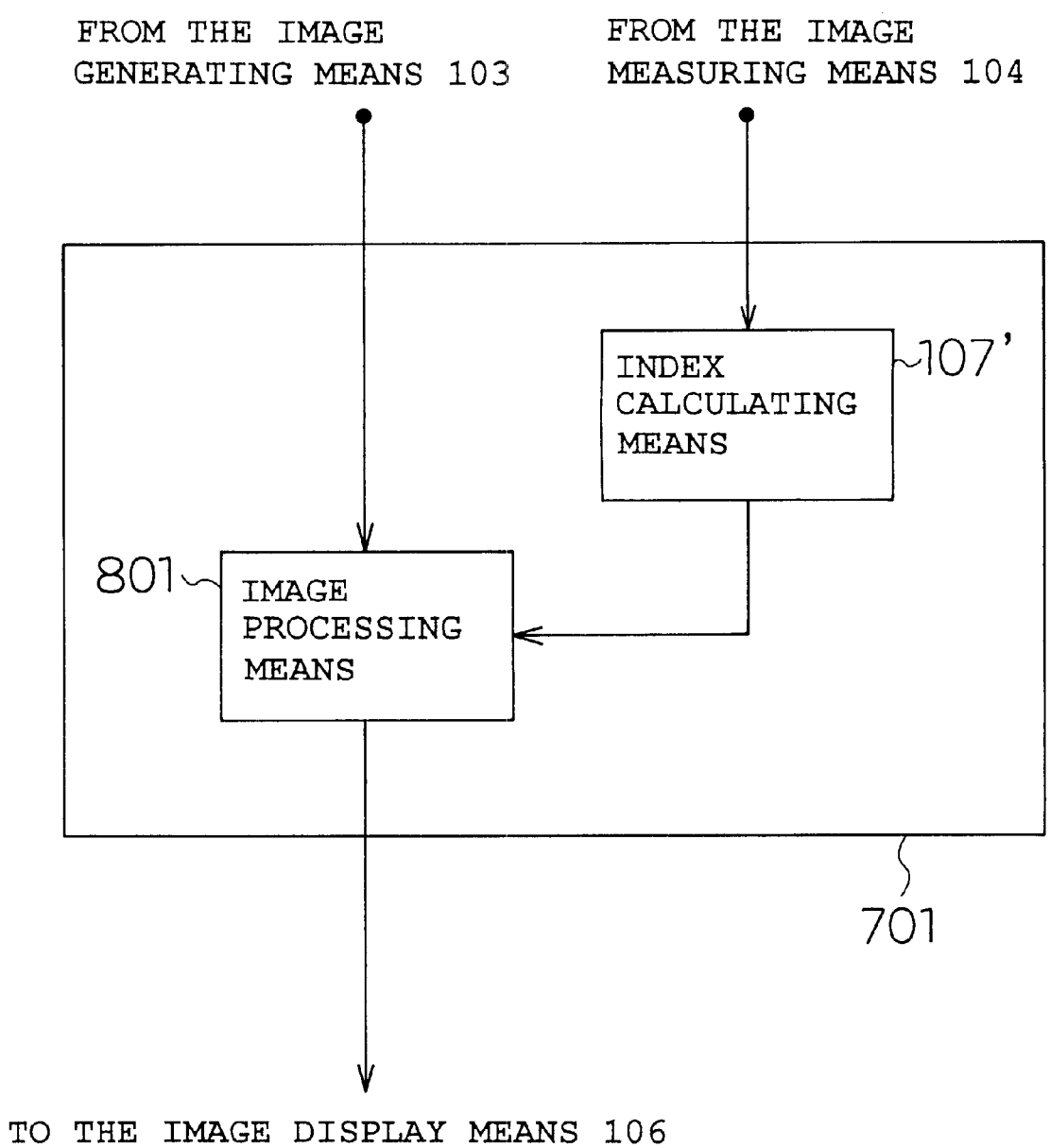
FIG. 8 is a block diagram showing an internal configuration of image correcting means 701.

Next, FIG. 8 is a block diagram showing internal configurations of the image correcting means 701 of the ultrasonic image generating apparatus. In FIG. 8, index calculating means 107' receives measured values of the brightness values, and calculates the sum, average, variance of the brightness values, standard deviation, histogram, cumulative frequency, image contrast values and so on thereof as the image indexes. Image processing means 801 processes the image outputted from the image generating means 103 based on the image indexes.

The operation of the ultrasonic image generating apparatus according to the fifth embodiment of the invention having the above configuration will be described below, and one embodiment of the ultrasonic image generating method of the present invention will also be described thereby. However, the same portions as in the fourth embodiment will be omitted, and the differences will be mainly described.

Although the amplification factor of the amplifying means is controlled based on the brightness in the fourth embodiment, it cannot be determined whether or not the inspection object exists only from the sum or average of the brightness values.

Thus, in this embodiment, the image correcting means 701 processes the image based on the brightness values and by using the indexes such as the standard deviation and variance mentioned later so as to realize distinction between the inspection object and noise and perform a correction of suppressing the noise.

First, a method of image adjustment by using the histogram or cumulative frequency will be described by referring to FIGS. 9 to 11.

The index calculating means 107' can estimate the image quality of the image data to an extent by examining the histogram or cumulative frequency of the brightness values as to the small areas shown in FIG. 5A or the entire image data. In addition, it can change the image quality by manipulating the histogram.

Here, FIG. 9A shows the histogram of the entire image data with reference to the brightness values, and FIG. 9B shows distribution of the cumulative frequencies corresponding to the histogram.

As shown in FIG. 9A, in the case where the histogram shows a gentle slope of distribution with one brightness value as a peak, the cumulative frequencies are as shown in FIG. 9B.

Next, FIG. 10A shows an ideal histogram of the entire image data, and FIG. 10B shows the distribution of the cumulative frequencies corresponding to the histogram.

To render the distribution of the cumulative frequencies shown in FIG. 9B close to the shape in FIG. 10B, a process is performed. The distribution of the brightness values shown in FIG. 9B should be changed. For instance, all the pixels having the brightness value "5" are manipulated to change the brightness value to 8 so that the shape of the distribution curve of the cumulative frequencies can be rendered close to FIG. 10B.

Figure 9:
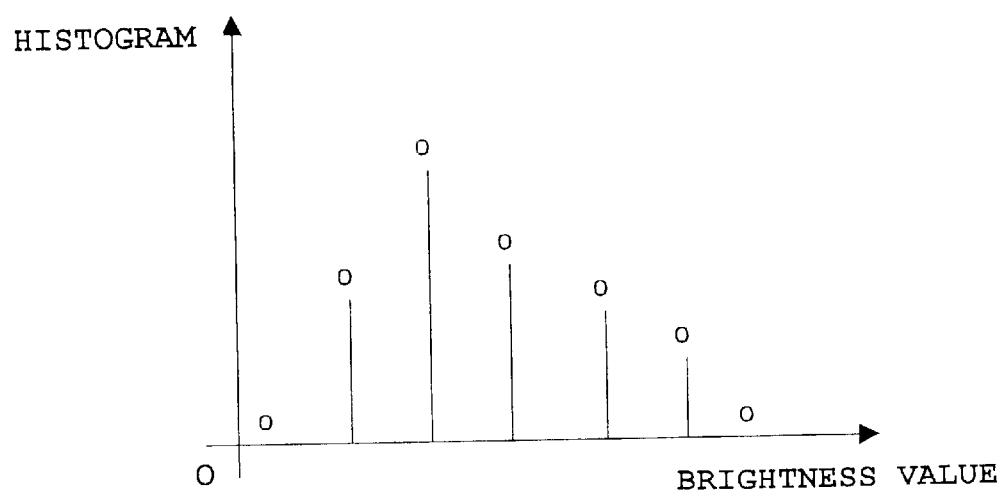
FIG. 9A is a diagram for explaining the method of image adjustment by the index calculating means 107 of using a histogram and a cumulative frequency of brightness values as the image indexes in the ultrasonic image generating apparatus according to the fifth embodiment.
FIG. 9B is a diagram for explaining the method of image adjustment by the index calculating means 107 of using the histogram and cumulative frequency of the brightness values as the image indexes in the ultrasonic image generating apparatus according to the fifth embodiment.
Figure 9:
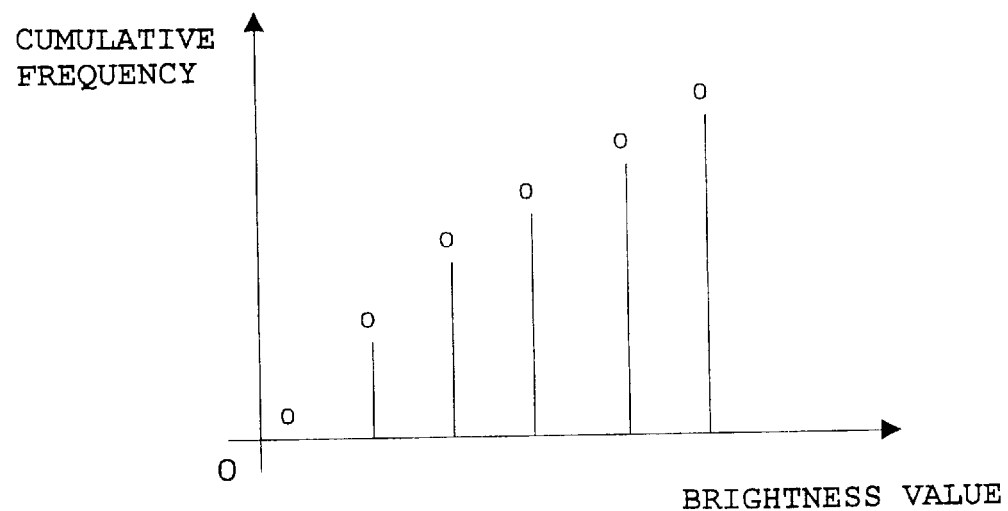
Figure 10:
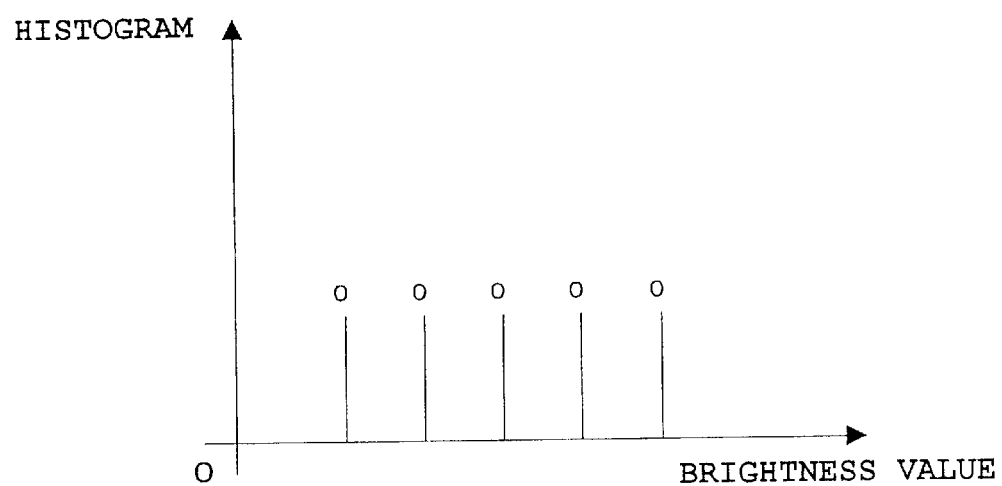
FIG. 10A is a diagram showing an ideal histogram in the image adjustment by the index calculating means 107 of using the histogram and cumulative frequency of the brightness values as the image indexes in the ultrasonic image generating apparatus according to the fifth embodiment.
FIG. 10B is a diagram showing the cumulative frequency corresponding to the ideal histogram in the image adjustment by the index calculating means 107 of using the histogram and cumulative frequency of the brightness values as the image indexes in the ultrasonic image generating apparatus according to the fifth embodiment.
Figure 10:
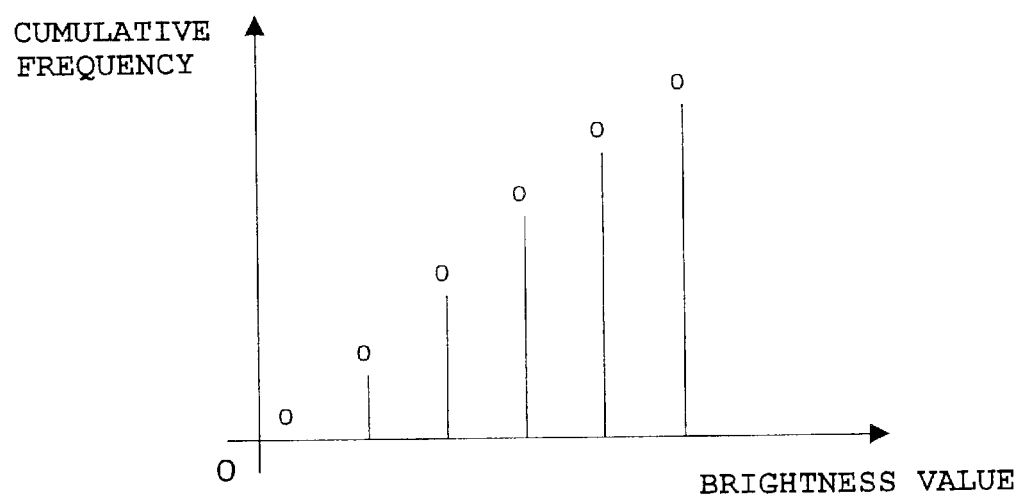
Figure 11A:
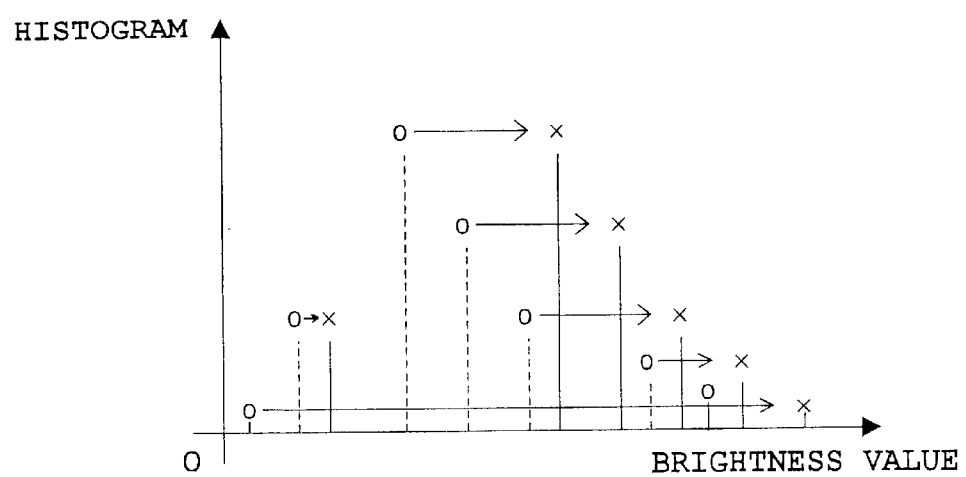
FIG. 11A is a diagram for explaining the method of image adjustment by the index calculating means 107 of using the histogram and cumulative frequency of the brightness values as the image indexes in the ultrasonic image generating apparatus according to the fifth embodiment.
Figure 11B:
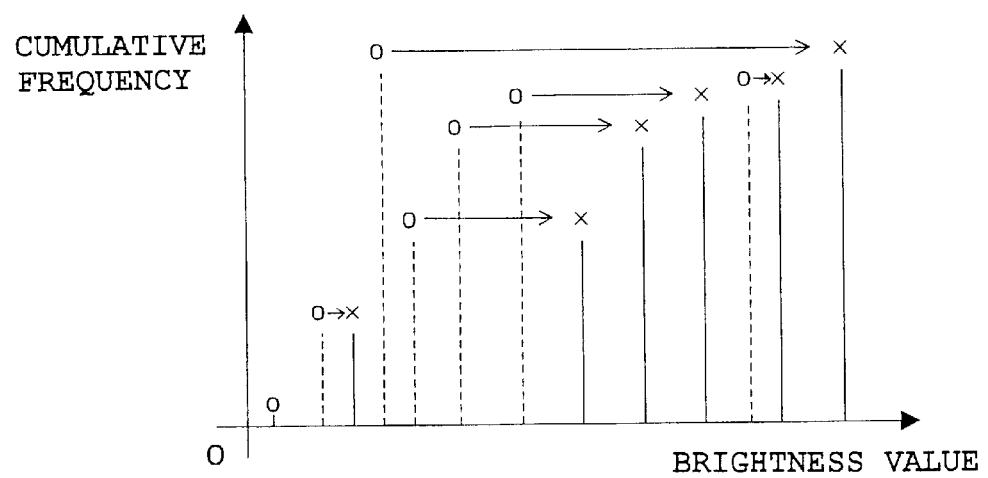
FIG. 11B is a diagram for explaining the method of image adjustment by the index calculating means 107 of using the histogram and cumulative frequency of the brightness values as the image indexes in the ultrasonic image generating apparatus according to the fifth embodiment.

Here, FIGS. 11A and 11B show the examples of changing the histograms and cumulative frequencies of FIGS. 9A and 9B. In the drawings, "◯" is the value before the change, and "×" indicates the value after the change. However, the values before the change in FIG. 11 are more exaggerated than those in FIG. 9 for explanation purposes.

In the case of FIGS. 11A and 11B, the brightness values of a large count (the number of the pixels having the same brightness value in the image) are deviated to the right, that is, in the direction of increasing the brightness values, and the differences (spacing of the horizontal axis) of the brightness values are rendered smaller as the count decreases so that the distribution shown in FIG. 11B is obtained and it becomes possible to render the distribution of the cumulative frequencies close to that shown in FIG. 10B.

Next, the method of image adjustment wherein the index calculating means 107' automatically determines whether the image is the inspection object or the noise by using the histogram will be described. As in the above case, the histogram of the brightness values is acquired as to the small areas shown in FIG. 5A or the entire image data.

The statistical indicators such as the variance and standard deviation are acquired for this histogram, and it is thereby clarified whether the noted area of the image includes the inspection object or is occupied by the noise so as to determine suitability/unsuitability of the image quality.

For instance, in the case where the standard deviation or the variance is smaller than a certain predetermined value, it means that the entire image is comprised of a large number of brightness values, and so it can be determined that clear contrast has not been obtained.

In the case of the ultrasonic image, the purpose is often extraction of the outline of the inspection object, and thus it is desirable that the brightness values are large in the outline portion and small in the other portions or are significantly different between the outline portion and the other portions. To be more specific, if the pixels of high brightness center on the outline portion and the pixels of low brightness center on the other portions, the distinction between the inspection object and noise becomes easier and the inspection object can be easily extracted by suppressing the noise.

Figure 12:
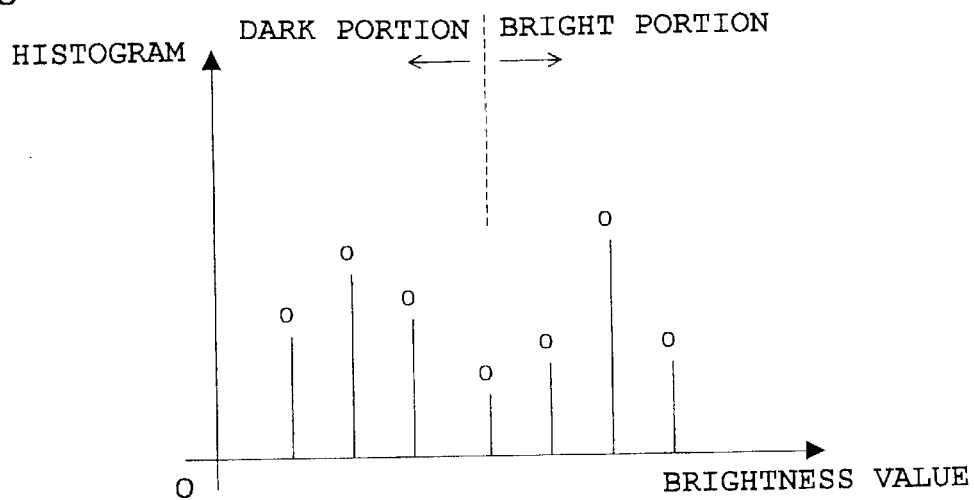
FIG. 12A is a diagram for explaining a method of automatically improving a contrast of an image by the index calculating means 107 by using standard deviation or variance as the image index in the ultrasonic image generating apparatus according to the fifth embodiment.
FIG. 12B is a diagram for explaining the method of automatically improving the contrast of the image by the index calculating means 107 by using the standard deviation or variance as the image index in the ultrasonic image generating apparatus according to the fifth embodiment.
FIG. 12C is a diagram for explaining the method of automatically improving the contrast of the image by the index calculating means 107 by using the standard deviation or variance as the image index in the ultrasonic image generating apparatus according to the fifth embodiment.
Figure 12:
Figure 12:
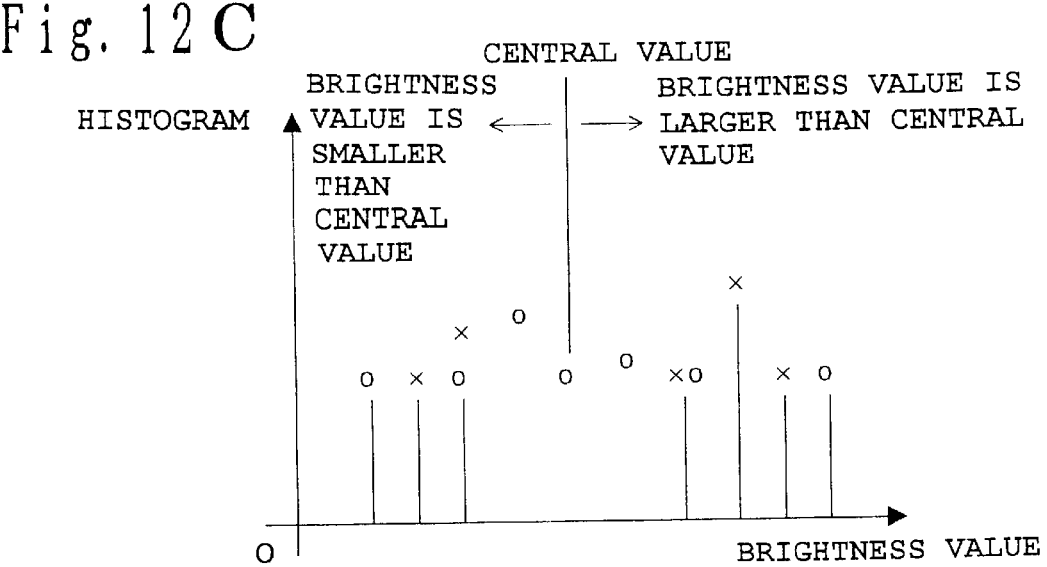

FIG. 12A shows an example of the histogram in this case. As for the brightness values, there is a group divided on a boundary of a certain brightness value into two portions of a higher portion and a lower portion.

On the other hand, the histogram shown in FIG. 12B indicates that the distribution of the brightness values is uniform, which is the image not having acquired the entire contrast. At this time, the standard deviation to the histogram in FIG. 12B is a very small value compared to the standard deviation to the histogram in FIG. 12A. Inversely speaking, the small standard deviation to the histogram means that the image has low contrast.

Thus, the histogram is manipulated in order to improve the contrast. A reference brightness value is arbitrarily set by using the average or a central value and so on, and the areas having the brightness values larger than this reference brightness value have them converted into still larger values, and the areas having the brightness values equal to or smaller than this reference brightness value have them converted into still smaller values.

FIG. 12C shows the histogram obtained by performing the above manipulation to the histogram in FIG. 12B. In the drawing, "◯" is the value before the manipulation, and "×" is the value after the manipulation.

The same histogram as that in FIG. 12A is obtained by performing this manipulation, and thus the image has the bright portions (of which brightness values are large) and the dark portions (of which brightness values are small) clearly separated with improved contrast so that the inspection object can be easily extracted. In addition, the standard deviation also becomes a larger value than that of the original image.

In addition, in the case where the standard deviation or the variance is smaller than the predetermined value and the average of the brightness values of the noted area is smaller than the predetermined value, that area may be determined to be the area in which no inspection object has been extracted. In such a case, no process is performed because, even if the histogram and the amplification factor are manipulated for the area, only the noise is processed and so it does not lead to clear depiction of the inspection object and deteriorates the image quality in addition.

Moreover, the series of manipulations can be performed by a predetermined function or a LUT (Look UP Table).

In addition, the above embodiment was described on the assumption that the image is directly processed and corrected by the standard deviation or the variance. Although it is meaningless to directly feed back the value of the standard deviation or the variance to the amplification factor, the standard deviation or the variance may be the material of determining whether or not the image displayed by this value is suitable.

To be more specific, in the fourth embodiment, it is possible, by using the index calculating means 107' instead of the index calculating means 107, to control the amplification factor in the amplification factor controlling means 105 based on the determination using the standard deviation or the variance.

In this case, the determination is made by the amplification factor controlling means 105, and it is necessary to set the parameter therefor.

In the amplification factor controlling means 105, the parameter as a determination reference may be determined by the user, or it may also be set as a fixed value or a dynamically changing value according to the body part as the imaging subject, the ultrasonic probe connected to the ultrasonic image generating apparatus in use, the amplification factor and focus depth. In particular, in the latter case, it is possible, with a predetermined type of the ultrasonic probe, to specify the imaging subject in the case of paying attention to a predetermined depth of a predetermined object, and so it has the effect of, as clinical knowledge, clarifying the position of the picked-up image at which the inspection object will be depicted.

In addition, it is also feasible for the amplification factor controlling means 105 described above to have the configuration of performing both the correction of the image and the control of the amplification factor.

(Sixth Embodiment)

Figure 13:
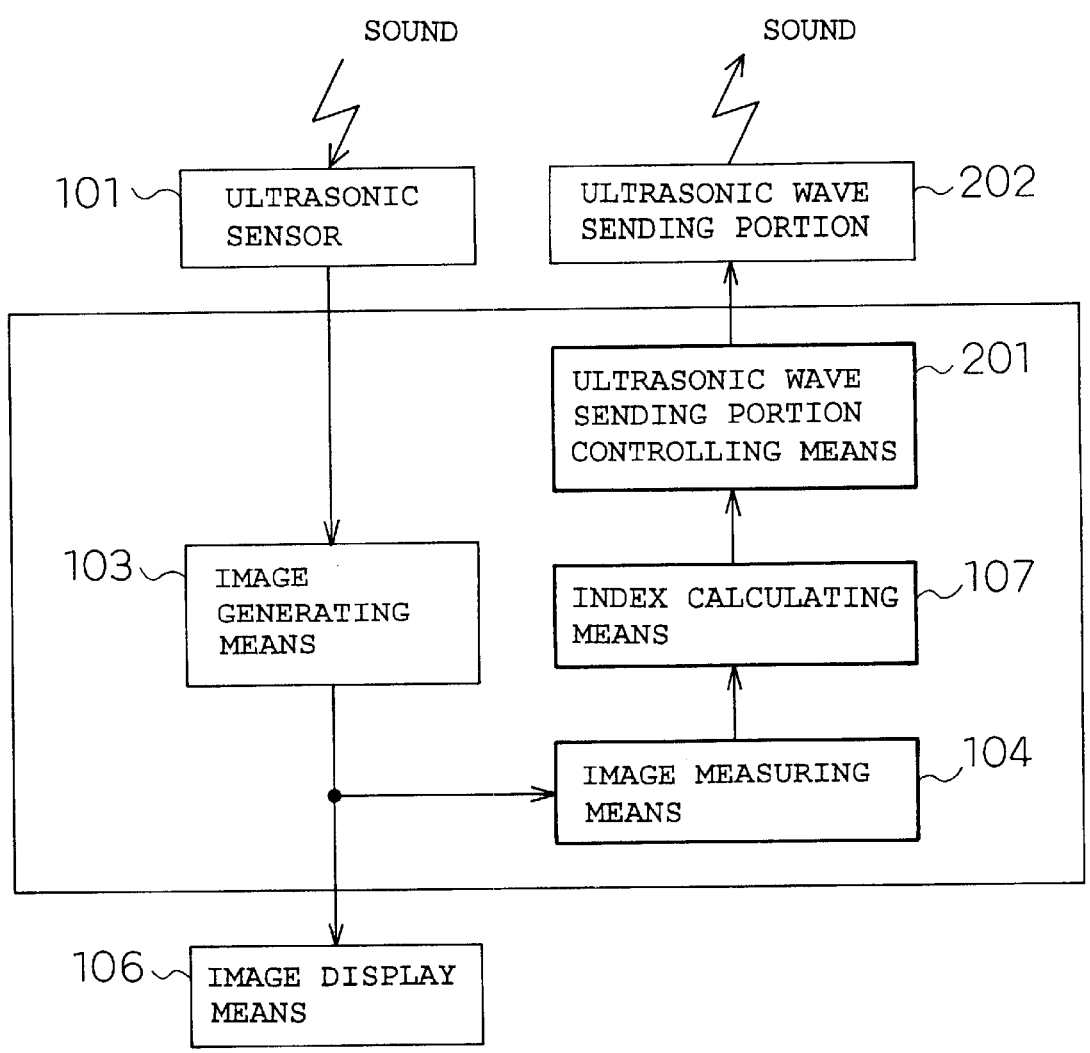
FIG. 13 is a block diagram showing a configuration of the ultrasonic image generating apparatus according to a sixth embodiment of the present invention.

FIG. 13 shows a schematic block diagram of the ultrasonic image generating apparatus according to a sixth embodiment of the present invention.

In FIG. 13, the portions which are the same as or equivalent to those in FIG. 1 are given the same reference numerals, and detailed description thereof will be omitted.

In addition, an ultrasonic wave sending portion 202 is means of outputting the sound signal to the object, and outputs the sound signal while moving as if scanning the object so as to allow a two-dimensional image to be obtained from a one-dimensional signal received by the ultrasonic sensor 101. Ultrasonic wave sending portion controlling means 201 is means of controlling the sound signal outputted by the ultrasonic wave sending portion 202 based on the output from the index calculating means 107.

While this embodiment is the same as the fourth embodiment to the extent that the image measuring means 104 measures the brightness values from the image generated by the image generating means 103, and the index calculating means 107 receives the brightness values measured by the image measuring means 104 and calculates the sum and average thereof as the image indexes, it is different in that it controls the ultrasonic wave sending portion controlling means 201 based on the image indexes to change the size of the sound signal to be outputted.

The operation of the ultrasonic image generating apparatus according to the sixth embodiment of the invention having the above configuration will be described below, and one embodiment of the ultrasonic image generating method of the present invention will also be described thereby.

First, the ultrasonic wave sending portion 202 outputs the sound signal to be the initial value to the object, and the sound signal reflected from the object is received by the ultrasonic sensor 101. The received sound signal is sent to the image generating means 103, where the image is generated from the sound information. The image data is written to the storage device such as the frame memory. The image measuring means 104 measures the brightness value for the generated image. The measured value is sent to the ultrasonic wave sending portion controlling means 201, and the ultrasonic wave sending portion 202 is controlled according to the measured value so as to control the sound sent toward the subject. The image display means 106 displays the image data in the frame memory of the image generating means.

In addition, the index calculating means 107 receives the measured value of the brightness value, and calculates the sum and average thereof as the image indexes and sends them to the ultrasonic wave sending portion controlling means 201. The image indexes are processed as in the fourth embodiment.

On receiving the image indexes, the ultrasonic wave sending portion controlling means 201 processes the information based on them, and issues to the ultrasonic wave sending portion 202 an order of changing the output of the sound signal to be sent. The methods of changing the output includes the method of changing the number of the elements used for beam forming.

As shown in FIGS. 5A and 5B, in the case where the sum or the average of the brightness values is lower than the predetermined value α or β as to the image data divided into the small areas, the control is performed to render the output of the sound signal higher, and in the case it is higher, the control is performed to render the output lower.

In compliance with the order from the ultrasonic wave sending portion controlling means 201, the ultrasonic wave sending portion 202 outputs the sound signal of which size is changed from the initial value. Thereafter, the same operation is repeated, and the ultrasonic image is generated a plurality of times until an adequate image is obtained.

It is possible, by thus operating, to extract an echo signal which is buried in a noise component due to weak output of the sound signal to be sent so as to consequently obtain the contrast on the displayed screen.

Figure 14:
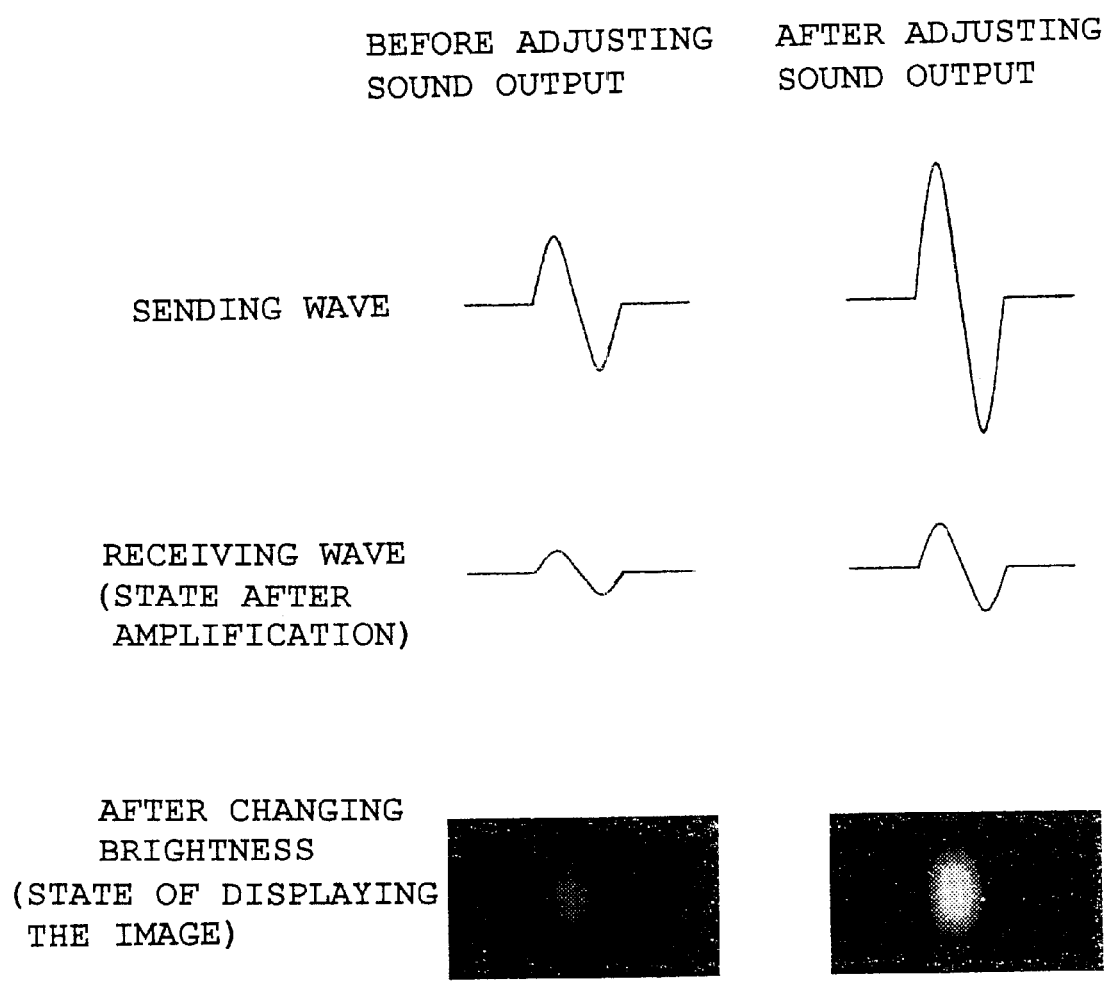
FIG. 14 is a diagram showing the effect of using a ultrasonic wave sending portion controlling means of the ultrasonic image generating apparatus according to the sixth embodiment of the present invention.

FIG. 14 is a diagram of the effect of being displayed on the screen after the brightness conversion in the case where the output of the sound signal to be sent is controlled by using the ultrasonic wave sending portion controlling means 201.

In addition, it is also possible to perform the adjustment of sound output as above for a plurality of image areas in the same image each time. To be more specific, in case of generating the image wherein, of the measurement subjects, the portion more distant from the ultrasonic sensor 101 is clearer, ultrasonic output is rendered weaker (decrease the number of elements transmitting the ultrasonic wave) in the portions close to the ultrasonic sensor 101 and the ultrasonic wave sending portion 202 and rendered stronger (increase the number of elements transmitting the ultrasonic wave) in the portions far therefrom so that the target body part is rendered as the image with more emphasis. Lastly, the images of the respective emphasized portions are synthesized into one piece so as to obtain an entirely clear image.

Next, the inventions implemented by the inventor hereof in relation to the present invention will be described below.

(Invention 1)

An ultrasonic image generating apparatus having:

receiving means of receiving an ultrasonic wave obtained from an object;

amplifying means of amplifying a signal received by the above described receiving means;

image generating means of generating an image based on a position at which the amplified signal of the above described amplifying means is plotted and the size of the above described signal at that position;

brightness measuring means of measuring brightness of the image generated by the above described image generating means; and controlling means of controlling an amplification factor of the above described amplifying means based on the brightness measured by the above described brightness measuring means.

(Invention 2)

An ultrasonic image generating apparatus having:

transmitting means of transmitting an ultrasonic wave to an object;

receiving means of receiving the ultrasonic wave obtained from the above described object;

image generating means of generating an image based on a position at which a signal received by the above described receiving means is plotted and the size of the above described signal at that position;

brightness measuring means of measuring brightness of the image generated by the above described image generating means; and controlling means of controlling the power of output of the above described transmitting means based on the brightness measured by the above described brightness measuring means.

(Invention 3)

The ultrasonic image generating apparatus according to invention 1 or 2, wherein the above described controlling means has index calculating means of calculating image indexes based on the brightness measured by the above described brightness measuring means, and controls the above described amplification factor or the power of output based on the above described image indexes.

(Invention 4)

The ultrasonic image generating apparatus according to invention 3, wherein the above described index calculating means calculates the sum and/or average of the brightness values as the above described image indexes.

(Invention 5)

The ultrasonic image generating apparatus according to invention 1 or 2, wherein the above described brightness measuring means measures the above described brightness of more arbitrary areas than those obtained by dividing the above described image into one or a plurality.

(Invention 6)

An ultrasonic image generating apparatus having:

receiving means of receiving an ultrasonic wave obtained from an object;

amplifying means of amplifying a signal received by the above described receiving means;

image generating means of generating an image based on a position at which an amplified signal of the above described amplifying means is plotted and the size of the above described signal at that position; and noise suppressing means of calculating all or a part of the sum, average, standard deviation, variance, contrast values, histogram and cumulative frequencies of brightness values obtained from the image generated by the above described image generating means and suppressing noise of the above described image based on them.

(Invention 7)

The ultrasonic image generating apparatus according to invention 6, wherein the above described noise suppressing means performs the suppression of the above described noise for more arbitrary areas than those obtained by dividing the above described image into one or a plurality.

(Invention 8)

The ultrasonic image generating apparatus according to any one of inventions 1 to 7 having image display means of displaying the image generated by the above described image generating means.

(Invention 9)

An ultrasonic image generating method having:

a receiving step of receiving an ultrasonic wave obtained from an object;

an amplifying step of amplifying a signal received by the above described receiving means;

an image generating step of generating an image based on a position at which a signal amplified by the above described amplifying step is plotted and the size of the above described signal at that position;

a brightness measuring step of measuring brightness of the image generated by the above described image generating step; and a controlling step of controlling an amplification factor of the above described amplifying step based on the brightness measured by the above described brightness measuring step.

(Invention 10)

An ultrasonic image generating method having:

a transmitting step of transmitting the ultrasonic wave to an object;

a receiving step of receiving an ultrasonic wave obtained from the above described object;

an image generating step of generating an image based on a position at which the signal received by the above described receiving step is plotted and the power of the above described signal at that position;

a brightness measuring step of measuring brightness of the image generated by the above described image generating step; and a controlling step of controlling the size of ultrasonic output of the above described transmitting step based on the brightness measured by the above described brightness measuring step.

(Invention 11)

An ultrasonic image generating method having:

a receiving step of receiving the ultrasonic wave obtained from an object;

an amplifying step of amplifying a signal received by the above described receiving step;

an image generating step of generating an image based on the position at which a signal amplified by the above described amplifying step is plotted and the size of the above described signal at that position; and a noise suppressing step of calculating all or a part of the sum, average, standard deviation, variance, contrast values, histogram and cumulative frequencies of the brightness values obtained from the image generated by the above described image generating step and suppressing the noise of the above described image based on them.

(Invention 12)

The ultrasonic image generating method according to any one of inventions 9 to 11 having an image display step of displaying the image generated by the above described image generating step.

(Invention 13)

A program of causing a computer to execute all or a part of the ultrasonic image generating method according to invention 9 having:

a receiving step of receiving the ultrasonic wave obtained from an object;

an amplifying step of amplifying a signal received by the above described receiving step;

an image generating step of generating an image based on the position at which the signal amplified by the above described amplifying step is plotted and the size of the above described signal at that position;

a brightness measuring step of measuring brightness of the image generated by the above described image generating step; and a controlling step of controlling an amplification factor of the above described amplifying step based on the brightness measured by the above described brightness measuring step.

(Invention 14)

A program of causing a computer to execute all or a part of the ultrasonic image generating method according to invention 10 having:

a transmitting step of transmitting the ultrasonic wave to an object;

a receiving step of receiving an ultrasonic wave obtained from the above described object;

an image generating step of generating an image based on the position at which a signal received by the above described receiving step is plotted and the power of the above described signal at that position;

a brightness measuring step of measuring brightness of the image generated by the above described image generating step; and a controlling step of controlling the size of ultrasonic output of the above described transmitting step based on the brightness measured by the above described brightness measuring step.

(Invention 15)

A program of causing a computer to execute all or a part of the ultrasonic image generating method according to invention 11 having:

a receiving step of receiving the ultrasonic wave obtained from an object;

an amplifying step of amplifying a signal received by the above described receiving step;

an image generating step of generating an image based on a position at which a signal amplified by the above amplifying step is plotted and the size of the above described signal at that position; and a noise suppressing step of calculating all or a part of the sum, average, standard deviation, variance, contrast values, histogram and cumulative frequencies of brightness values obtained from the image generated by the above described image generating step and suppressing noise of the above described image based on them.

(Invention 16)

A medium processable by a computer and having a program of causing the computer to execute all or a part of the ultrasonic image generating method according to invention 9 having:

a receiving step of receiving the ultrasonic wave obtained from an object;

an amplifying step of amplifying a signal received by the above described receiving step;

an image generating step of generating an image based on the position at which a signal amplified by the above described amplifying step is plotted and the size of the above described signal at that position;

a brightness measuring step of measuring brightness of the image generated by the above described image generating step; and a controlling step of controlling an amplification factor of the above described amplifying step based on the brightness measured by the above described brightness measuring step.

(Invention 17)

A medium processable by a computer and having a program of causing the computer to execute all or a part of the ultrasonic image generating method according to invention 10 having:

a transmitting step of transmitting the ultrasonic wave to an object;

a receiving step of receiving an ultrasonic wave obtained from the above described object;

an image generating step of generating an image based on a position at which a signal received by the above described receiving step is plotted and the size of the above described signal at that position;

a brightness measuring step of measuring brightness of the image generated by the above described image generating step; and a controlling step of controlling the size of ultrasonic output of the above described transmitting step based on the brightness measured by the above described brightness measuring step.

(Invention 18)

A medium processable by a computer and having a program of causing the computer to execute all or a part of the ultrasonic image generating method according to invention 11 having:

a receiving step of receiving an ultrasonic wave obtained from an object;

an amplifying step of amplifying a signal received by the above described receiving step;

an image generating step of generating an image based on a position at which a signal amplified by the above described amplifying step is plotted and the size of the above described signal at that position; and a noise suppressing step of calculating all or a part of the sum, average, standard deviation, variance, contrast values, histogram and cumulative frequencies of brightness values obtained from the image generated by the above described image generating step and suppressing noise of the above described image based on them.

The above inventions are characterized by calculating the pixel values for the image data and changing an output level of the sound to be transmitted so as to improve an S/N ratio of the received signal.

In addition, the amplification factor of the received signal is modified to change a dynamic range of the pixel values of the image and histogram distribution of the pixel values so as to improve the image quality. Furthermore, the above adjustment is performed to be closer to the dynamic range and histogram distribution of the pixel values preset according to the measurement results so as to implement automation of image quality adjustment.

Moreover, in the above fourth to sixth embodiments, the ultrasonic sensor 101 is equivalent to the receiving means of the above inventions, the ultrasonic wave sending portion 202 is equivalent to the transmitting means thereof, and the image measuring means 104 is equivalent to the brightness measuring means thereof, the amplification factor controlling means 105 and the index calculating means 107 are equivalent to the controlling means of the above first invention, the ultrasonic wave sending portion controlling means 201 and the index calculating means 107 are equivalent to the controlling means of the above second invention, and the image correcting means 701 is equivalent to the noise suppressing means of the above inventions. In addition, the index calculating means 107 is equivalent to the index calculating means of the above inventions.

In addition, while the above inventions were described as having the image display means 106, the above inventions may also be implemented with the image display means as a separate configuration.

In addition, the above inventions are the program of causing the computer to execute all or a part of the steps of the above-mentioned ultrasonic image generating method of the above inventions, which is the program operating in synergy with the computer.

In addition, the above inventions are the medium having the program of causing the computer to perform all or a part of the operations of all or a part of the steps of the above-mentioned ultrasonic image generating method of the above inventions, which can be read by the computer and has the read program operate in synergy with the computer to implement the above described operations.

Moreover, a part of the steps of the above inventions above refers to some of a plurality of the steps thereof or a certain operation in one step.

In addition, the record medium readable to the computer and having recorded the program of the above inventions is also included in the above inventions.

In addition, one form of using the program of the above inventions may also be an aspect of being recorded on the record medium readable to the computer and operating in synergy with the computer.

In addition, one form of using the program of the above inventions may also be an aspect of being transmitted in a transmission medium, read by the computer and operating in synergy with the computer.

In addition, the data structures of the above inventions include a database, a data format, a data table, a data list, a data type and so on.

In addition, the record media include a ROM and so on, and the transmission media include transmission mechanisms such as the Internet, light, radio wave, sound wave and so on.

In addition, the above-mentioned computer of the above inventions is not limited to sheer hardware such as a CPU but may also include firmware, an OS and even peripherals. Moreover, as described above, the configuration of the above inventions may be implemented either as software or as hardware.

As described above, according to the above inventions, it is possible to adjust the image quality of the displayed image in real time and automatically in ultrasonic image generation. In addition, it is also possible to automatically perform the work of image adjustment which required experience in the past.

As described above, according to the present invention, it is possible to obtain the ultrasonic image generating apparatus and so on capable of thoroughly obtaining the image in the imaging area while saving time and effort for operation on the user side and reducing the area where the ultrasonic wave is shielded by the object.

What is claimed is:

1. An ultrasonic image generating apparatus comprising:
   ultrasonic beam outputting means of outputting an ultrasonic beam to a predetermined subject area;
   ultrasonic beam receiving means of receiving a reflected ultrasonic beam which is a reflected wave of said ultrasonic beam obtained from said subject area;
   image generating means of generating an image based on the reflected ultrasonic beam received by said ultrasonic beam receiving means;
   image analyzing means of analyzing the image generated by said image generating means; and
   ultrasonic beam output direction controlling means of performing control of changing an outgoing direction of the ultrasonic beam of said ultrasonic beam outputting means to said subject area;
   wherein the ultrasonic beam output direction controlling means controls said change based on analysis results of said image analyzing means;
   wherein said image analyzing means analyzes whether or not there is a predetermined imaging target in said subject area, and in the case where there is said imaging target, analyzes whether or not there is a shielded area in which said ultrasonic beam is shielded by said imaging target in said subject area, and
   in the case where there is said shielded area, said ultrasonic beam output direction controlling means controls said change so that the area to be passed through by the ultrasonic beam emitted from said ultrasonic beam outputting means includes a part of said shielded area.

2. The ultrasonic image generating apparatus according to claim 1, wherein said ultrasonic beam output direction controlling means electrically controls said change.

3. A medium having a program of causing a computer to function as the image analyzing means of analyzing the image generated by said image generating means of the ultrasonic image generating apparatus according to claim 1 and the ultrasonic beam output direction controlling means of controlling said change based on the analysis results of said image analyzing means, and said program processable by a computer.

4. An ultrasonic image generating apparatus comprising:
   ultrasonic beam outputting means of outputting an ultrasonic beam to a predetermined subject area;
   ultrasonic beam receiving means of receiving a reflected ultrasonic beam which is a reflected wave of said ultrasonic beam obtained from said subject area;
   image generating means of generating an image based on the reflected ultrasonic beam received by said ultrasonic beam receiving means;
   reflected ultrasonic beam analyzing means of analyzing the reflected ultrasonic beam received by said ultrasonic beam receiving means; and
   ultrasonic beam output direction controlling means of performing control of changing an outgoing direction of the ultrasonic beam of said ultrasonic beam outputting means to said subject area;
   wherein said ultrasonic beam output direction controlling means controls said change based on alaysis results of said reflected ultrasonic beam analyzing means;
   wherein said reflected ultrasonic beam analyzing means analyzes whether or not there is a non-detected area in which no reflected ultrasonic beam is detected in said subject area, and
   in the case where there is said non-detected area, said ultrasonic beam output direction controlling means controls said change so that the area to be passed through by the ultrasonic beam emitted from said ultrasonic beam outputting means next includes a part of said non-detected area.

5. The ultrasonic image generating apparatus according to claim 4,
   wherein said subject area is determined to be within a distance capable of detecting said reflected ultrasonic beam at a predetermined intensity.

6. A medium having a program of causing a computer to function as the reflected ultrasonic beam analyzing means of analyzing the reflected ultrasonic beam received by said ultrasonic beam receiving means of the ultrasonic image generating apparatus according to claim 4 and the ultrasonic beam output direction controlling means of controlling said change based on the analysis results of said reflected ultrasonic beam analyzing means, and said program processable by a computer.

7. An ultrasonic image generating method comprising:
   an ultrasonic beam outputting step of outputting an ultrasonic beam to a predetermined subject area;
   an ultrasonic beam receiving step of receiving a reflected ultrasonic beam which is a reflected wave of said ultrasonic beam obtained from said subject area;
   an image generating step of generating an image based on the reflected ultrasonic beam received by said ultrasonic beam receiving step;
   an image analyzing step of analyzing the image generated by said image generating step, and wherein the ultrasonic beam output direction controlling step controls said change based on analysis results thereof; and
   an ultrasonic beam output direction controlling step of performing control of changing an outgoing direction of the ultrasonic beam of said ultrasonic beam outputting step to said subject area;
   wherein said image analyzing step analyzes whether or not there is a predetermined imaging target in said subject area, and in the case where there is said imaging target, analyzes whether or not there is a shielded area in which said ultrasonic beam is shielded by said imaging target in said subject area, and in the case where there is said shielded area, said ultrasonic beam output direction controlling step controls said change so that the area to be passed through by the ultrasonic beam emitted from said ultrasonic beam outputting step includes a part of said shielded area.

8. The ultrasonic image generating method according to claim 7, wherein said ultrasonic beam output direction controlling step electrically controls said change.

9. An ultrasonic image generating method comprising:

an ultrasonic beam outputting step of outputting an ultrasonic beam to a predetermined subject area;

an ultrasonic beam receiving step of receiving a reflected ultrasonic beam which is a reflected wave of said ultrasonic beam obtained from said subject area;

an image generating step of generating an image based on the reflected ultrasonic beam received by said ultrasonic beam receiving step;

a reflected ultrasonic beam analyzing step of analyzing the reflected ultrasonic beam received by said ultrasonic beam receiving step, and wherein said ultrasonic beam output direction controlling step controls said change based on analysis results thereof; and an ultrasonic beam output direction controlling step of performing control of changing an outgoing direction of the ultrasonic beam of said ultrasonic beam outputting step to said subject area;

wherein said reflected ultrasonic beam analyzing step analyzes whether or not there is a non-detected area in which no reflected ultrasonic beam is detected in said subject area, and in the case where there is said non-detected area, said ultrasonic beam output direction controlling step controls said change so that the area to be passed through by the ultrasonic beam emitted from said ultrasonic beam outputting step next includes a part of said non-detected area.

* * * * *